United States Patent
Ollier et al.

(10) Patent No.: US 9,234,879 B2
(45) Date of Patent: Jan. 12, 2016

(54) DEVICE COMPRISING A FLUID CHANNEL PROVIDED WITH AT LEAST ONE MICRO OR NANOELECTRONIC SYSTEM AND METHOD FOR CARRYING OUT SUCH A DEVICE

(71) Applicant: COMMISSARIAT A L'ENERGIE ATOMIQUE ET AUX ENE ALT, Paris (FR)

(72) Inventors: Eric Ollier, Grenoble (FR); Carine Marcoux, Voiron (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 0 days.

(21) Appl. No.: 14/335,175

(22) Filed: Jul. 18, 2014

(65) Prior Publication Data

US 2015/0316517 A1 Nov. 5, 2015

(30) Foreign Application Priority Data

Jul. 22, 2013 (FR) ...................................... 13 57199

(51) Int. Cl.
*H01L 29/82* (2006.01)
*H01L 29/84* (2006.01)
(Continued)

(52) U.S. Cl.
CPC ............ *G01N 30/6095* (2013.01); *B01D 53/02* (2013.01); *B81C 1/00269* (2013.01); *G01N 30/64* (2013.01); *B81C 2203/0172* (2013.01); *H01L 2924/1461* (2013.01)

(58) Field of Classification Search
CPC .............................................. H01L 2924/1461
See application file for complete search history.

(56) References Cited

U.S. PATENT DOCUMENTS 6,936,902 B2 * 8/2005 Reichenbach et al. ........ 257/415
7,098,117 B2 * 8/2006 Najafi et al. .................. 438/456
(Continued)

FOREIGN PATENT DOCUMENTS

| EP | 1 362 827 A1 | 11/2003 |
| WO | WO 2006/078968 A2 | 7/2006 |
| WO | WO 2011/154363 | 12/2011 |

OTHER PUBLICATIONS

U.S. Appl. No. 14/336,351, filed Jul. 21, 2014, Ollier, et al.
(Continued)

*Primary Examiner* — Ida M Soward
(74) *Attorney, Agent, or Firm* — Oblon, McClelland, Maier & Neustadt, L.L.P.

(57) ABSTRACT

Device including a substrate including at least one microelectronic and/or nanoelectronic structure (NEMS) having a sensitive portion and a fluid channel. The fluid channel includes two lateral walls, an upper wall connecting the two lateral walls, a lower wall formed by the substrate, and at least two openings in order to provide a circulation in the fluid channel, with the openings being defined between the two lateral walls, with the structure being located inside the fluid channel. Electrical connection lines extend between the structure and the outside of the fluid channel, with the connection lines being carried out on the substrate and passing under the lateral walls. The device also includes an intermediate layer having a planar face in contact with base faces of said lateral walls. The connection lines are at least partially covered by the intermediate layer at least immediately above base faces of the lateral walls. The lateral walls are made sealingly integral on the substrate by a sealing layer on the intermediate layer.

28 Claims, 14 Drawing Sheets

(51) Int. Cl.
  *G01N 30/60* (2006.01)
  *G01N 30/64* (2006.01)
  *B01D 53/02* (2006.01)
  *B81C 1/00* (2006.01)

(56) References Cited

U.S. PATENT DOCUMENTS

| | | | |
|---|---|---|---|
| 7,381,583 B1* | 6/2008 | Ebel et al. | 438/53 |
| 7,544,531 B1* | 6/2009 | Grosjean | 438/50 |
| 7,803,665 B2* | 9/2010 | Witvrouw et al. | 438/124 |
| 8,062,497 B2* | 11/2011 | Witvrouw et al. | 205/118 |
| 8,101,458 B2* | 1/2012 | Kumar et al. | 438/106 |
| 8,507,358 B2* | 8/2013 | Chou | 438/452 |
| 8,692,337 B2* | 4/2014 | Berthelot et al. | 257/415 |
| 8,921,144 B2* | 12/2014 | Dunbar et al. | 438/50 |
| 8,946,831 B2* | 2/2015 | Liu et al. | 257/414 |
| 8,980,698 B2* | 3/2015 | Verheijden et al. | 438/125 |
| 8,999,762 B2* | 4/2015 | Baillin et al. | 438/124 |
| 2002/0022261 A1 | 2/2002 | Anderson et al. | |
| 2004/0087043 A1 | 5/2004 | Lee et al. | |
| 2005/0156260 A1* | 7/2005 | Partridge et al. | 257/414 |
| 2008/0122020 A1* | 5/2008 | Metz et al. | 257/415 |
| 2008/0283991 A1* | 11/2008 | Reinert | 257/685 |
| 2009/0065928 A1* | 3/2009 | Lutz et al. | 257/704 |
| 2011/0003422 A1* | 1/2011 | Katragadda et al. | 438/51 |
| 2012/0272742 A1 | 11/2012 | Andreucci et al. | |
| 2012/0321907 A1* | 12/2012 | Hoivik et al. | 428/615 |
| 2013/0061674 A1* | 3/2013 | Reichenbach et al. | 73/514.32 |
| 2013/0285171 A1* | 10/2013 | Najafi et al. | 257/415 |
| 2014/0015123 A1* | 1/2014 | Bowles et al. | 257/737 |
| 2014/0027927 A1* | 1/2014 | Reinmuth et al. | 257/774 |
| 2014/0158334 A1 | 6/2014 | Dellea et al. | |
| 2014/0162392 A1 | 6/2014 | Ollier et al. | |
| 2014/0166085 A1 | 6/2014 | Ollier | |
| 2014/0166463 A1* | 6/2014 | Jahnes et al. | 200/600 |
| 2015/0001990 A1 | 1/2015 | Ollier et al. | |
| 2015/0021720 A1* | 1/2015 | Ollier et al. | 257/415 |
| 2015/0041932 A1* | 2/2015 | Herrin et al. | 257/418 |

OTHER PUBLICATIONS

French Preliminary Search Report issued Mar. 28, 2014, in French Application No. 1357199 filed Jul. 22, 2013 (with English Translation of Categories of Cited Documents).
U.S. Appl. No. 14/514,703, filed Oct. 15, 2014, Ollier, et al.
U.S. Appl. No. 14/182,659, filed Feb. 18, 2014, Ollier.
"3D MEMS High Vacuum Wafer Level Packaging," S. Nicolas et al., *Electronic Components and Technology Conference*, May 29-Jun. 1, 2012, pp. 370-376.
"3-D Hyperintegration and Packaging Technologies for Micro-Nano Systems," Jian-Qiang Lu, *Proceedings of the IEEE*, vol. 97, No. 1, Jan. 2009, pp. 18-30.
"Thru-Wafer Interconnect for SOI-MEMS 3D Wafer-Level Hermetic Packing," Chiung-Wen Lin et al., *Solid-State Sensors, Actuators and Microsystems Conference*, 2007, Transducers 2007, International, pp. 2111-2114.

* cited by examiner

DEVICE COMPRISING A FLUID CHANNEL PROVIDED WITH AT LEAST ONE MICRO OR NANOELECTRONIC SYSTEM AND METHOD FOR CARRYING OUT SUCH A DEVICE

TECHNICAL FIELD AND PRIOR ART

This invention relates to a device comprising a fluid channel provided with at least one micro- or nanoelectronic system and a method for carrying out such a device.

The notions of microelectronic or nanoelectronic systems integrate microelectromechanical systems (MEMS) and nanoelectromechanical systems (NEMS). In a concern for simplification they will be referred to in the rest of the description as MEMS and NEMS. These systems are commonly used today in many products. New applications are appearing in particular due to the development of NEMS that offer new advantages thanks to the reduction in dimensions. In particular, due to the high sensitivity in mass of this type of systems, they are of great interest for chemical or biological sensors.

A NEMS or a MEMS comprises a fixed portion and at least one suspended portion (able to be mobile) or sensitive portion in relation to the fixed portion But for these applications in particular, it is necessary to manage the exposure of the structure of the MEMS or NEMS type, which offers particular physical-chemical characteristics, to a surrounding environment, in general gaseous or liquid. For this, the MEMS or NEMS sensitive structure is arranged in a fluid channel wherein the medium flows and allows for the putting into contact of the medium to be analysed with the NEMS or MEMS sensitive structure.

These sensitive structures are connected to an electronic signal collection and supply system via electric connections, with the latter connecting the structure to the electronic system located outside of the fluid channel.

The fluid channel is carried out by adding a cover on a substrate comprising the sensitive structure or structures. The cover is sealed tightly on the substrate and comprises at least two openings in order to provide the circulation in the channel of the fluid to be analysed. The cover is formed by a cavity carried out in a substrate of several μm to several hundreds of μm in depth for example.

Document WO2011/154363 describes a device for analysis, for example a gas chromatography microcolumn comprising MEMS and/or NEMS in the microcolumn, forming sensors. The connexion of the MEMS and/or NEMS is carried out example by vias.

The sealing of the cover can be of the polymer sealing, molecular sealing, anode sealing, eutectic sealing, glass frit, etc. type. Then the problem arises of carrying out electric connections between the sensitive structure or structures located inside the fluid channel and the outside of the fluid channel since the sealing, while still allowing for these electric connections, must be sealed.

A technique consists, after sealing the cover, in opening wide cavities in the thickness of the cover only above zones of metal pads in order to allow for a realisation of direct contact by wirebonding for these pads, each contact pad being surrounded by a sealing bead, for example made of polymer, in order to insulate this portion of the cavity. But this technique has the disadvantage of introducing additional patterns for these electrical passages inside the fluid channel which is not desirable because they can be at the origin of disturbance of the circulation of the fluid, generation of dead volumes, etc. Moreover, this technique is poorly suited in the case of sensitive structures of the NEMS or MEMS type because these structures require metal or semiconductor material contact pads of small size in order to reduce the parasitic capacities and be able to extract a useable electrical signal with a good signal-to-noise ratio. Finally, this technique is not suited for components formed from NEMS or MEMS in networks, as the latter are interconnected together with a substantial density, which entails implementing pads of very small size, and possibly using several metal levels.

Another technique for carrying out these electrical connections while still providing for the seal consists in carrying out connections of the Via type, for example TSVs (Through Silicon Via) or TGVs (Through Glass Via). Document "3D MEMS high vacuum wafer level packaging"—S. Nicolas and al. Electronic Components and Technology Conference (ECTC), 2012 IEEE 62nd, Date of Conference: May 29 2012-Jun. 1 2012, describes such achievements. For example, such connections of the TSV type would for example be carried out in the thickness of the cover and would open into the cavity, with the electrical continuity then being provided by a metal pad/bead inside the cavity. However such vias would be carried out in substantial thicknesses of semiconductor material, which can be of a magnitude of several hundreds of μm, which makes the manufacture of contacts of small size very difficult. In addition, the presence of TSVs passing through the cover and opening into the fluid cavity can disturb the operation of the fluid channel, for example by disturbing the propagation of the mixture in circulation, by disturbing the chemical properties of the interfaces in contact with the medium in circulation due to the materials of the TSVs, etc. In addition, in light of the dimensions of the channel, in particular of the height of the cavity, the electrical connection between the TSV in the cover and the sensitive structure would be difficult to carry out.

DESCRIPTION OF THE INVENTION

It is consequently a purpose of this invention to offer a device comprising at least one fluid channel, comprising one or several sensitive structures located in the fluid channel, and electric connections between the sensitive structure or structures located in the fluid channel and with the outside of the fluid channel not having the aforementioned disadvantages.

It is also a purpose to offer a method for carrying out such a structure with a fluid channel.

The aforementioned purpose is achieved by a structure comprising a fluid channel formed by a substrate comprising at least one sensitive structure, at least one electrical connection between the sensitive structure and a zone outside of the fluid channel, said electrical connection being formed on the surface of the substrate bearing the sensitive structure, an intermediate layer covering at least partially the electrical connection, said intermediate layer having a free face able to seal the cover, and a cover tightly sealed on the planar free face of the intermediate layer.

In this application, "face of the intermediate layer able to seal" means a face having a surface state that allows for the sealing with the base faces of the cover, for example a sealing par dry film, a molecular or eutectic sealing or by thermocompression. The face able to seal can have a certain roughness or a certain relief which nevertheless allows for the sealing.

Implementing an intermediate layer makes it possible to carry out the lateral connection lines while still providing a simplified carrying out of the seal between the cover and the substrate, since the sealing is carried out on the advantageously planar intermediate layer. Furthermore, as the electrical connection or connections are carried out on the surface of the substrate and covered by the intermediate layer, they do not disturb the flow contrary to the other aforementioned solutions, for example TSVs carried out in the cover.

In other terms, the fluid channel device comprises a layer that provides an encapsulation of the connection lines at least in the sealing zone with the cover, this layer then allows for the release of the NEMS/MEMS structure while still retaining a surface that allows for the sealing above the connection lines, with this surface being sufficiently planar to carry out a seal of the cover on the NEMS/MEMS structure.

The invention therefore makes it possible to avoid having recourse to the carrying out of vias through the cover and/or the opening of the wide cavities in the thickness of the cover in order to allow for a realisation of contact. The method for carrying out is therefore substantially simplified.

Very advantageously, this intermediate layer can be such that it encapsulates the materials of the NEMS or MEMS structure except for the sensitive portion which, through their presence in the fluid channel, could interact with the medium in circulation in the channel, i.e. it insulates the materials from the NEMS or MEMS structure other than the sensitive portion of the inside of the fluid channel. This is the case for example with metals or dielectrics which are implemented in the fluid channel if the mechanical structure is constituted of a dense NEMS network. In this case here, the intermediate layer is only open NEMS structures intended to interact with the surrounding environment.

Also very advantageously, the presence of the intermediate layer allows for the release of the mechanical structures before the sealing of the cover. This is particularly advantageous as it is possible to consider varied mechanical structure functionalisation layers implemented other than by liquid means. These functionalisation layers are much more compatible with released mechanical structures. They can be implemented, for example by vapour deposition or by evaporation, by epitaxy or any other method of forming, even by adding layers. Thanks to the invention, it is possible to deposit a functionalisation layer on the NEMS or MEMS structure and as such to functionalise them before sealing the cover on the substrate bearing the mechanical structures. In this case, the functionalisation layer can fully cover the suspended portion of the mechanical structures, thus offering an increased interaction surface between the environment and the functionalisation layer.

Preferably a dry film of resin is used to seal the NEMS portion comprising the intermediate layer and the cover.

Moreover, the structure according to the invention and the method for carrying it out allow for a collective carrying out of chips provided with a fluid channel, with the chips being separated by pre-cutting between the channels and pre-cutting transversal to the channels.

The subject-matter of the present invention thus is a device comprising a substrate comprising at least one microelectronic and/or nanoelectronic structure comprising at least one sensitive portion and a fluid channel defined between said substrate and a cover, said fluid channel comprising two lateral walls and an upper wall connecting the two lateral walls and a lower wall formed by said substrate and at least two openings in order to provide for a circulation in said channel, said microelectronic and/or nanoelectronic structure being located inside the fluid channel, at least one electrical connection line extending between said microelectronic and/or nanoelectronic structure and the outside of the fluid channel, said connection line being carried out on the substrate and passing under one of the lateral walls, said device further comprising an intermediate layer comprising a face in contact with base faces of said lateral walls, said face of the intermediate layer having an aptitude for sealing with the base faces, said connection line being at least partially covered by said intermediate layer at least immediately above the base face of said lateral wall, said lateral walls being fixed on said substrate by sealing on said intermediate layer.

For example, the device comprising at least one pair of connection lines extending laterally on either side of the microelectronic and/or nanoelectronic structure and each passing under a lateral wall.

In an embodiment, the intermediate layer covers, in the fluid channel, the entire microelectronic and/or nanoelectronic structure except for its sensitive portion.

The intermediate layer can comprise an electrical insulating material, such as a silicon oxide, or a silicon nitride.

In an advantageous method, the device comprises a functionalisation layer encapsulating at least one portion of the sensitive portion of the microelectronic and/or nanoelectronic structure. The functionalisation layer can comprise one or several materials chosen from among organic, or inorganic, materials, polymers, oxides, semiconductors. The functionalisation layer or layers can be carried out by chemical vapour deposition, by evaporation, epitaxy, porosification via etching, deposit by spray, spotting (depositing of drops), etc. It is particularly interesting to use porous materials as a functionalisation layer.

The device can comprise connection lines and contact pads, said contact pads being located outside of the fluid channel, said connection lines extending between the microelectronic and/or nanoelectronic structure and the contact pads.

In an embodiment, the connection lines comprise several levels of metallisation at least inside the channel.

The sealing can advantageously be carried out by means of a dry film for sealing inserted between the intermediate layer and the base faces of the lateral walls of the cover. The dry film is preferably a resin with epoxy, phenol, acrylic or silicone bases for example.

The dry sealing film can be structured in several beads on interfaces between the intermediate layer and the base faces of the lateral walls. Advantageously, the beads are substantially parallel to the fluid channel.

The device can further comprise at least one layer of material inserted between the intermediate layer and the base faces of the lateral walls creating a eutectic sealing, by thermocompression, or by screen printing.

The sealing can also be a molecular sealing, with then no interposition of material between the cover and the intermediate layer required.

In an embodiment, the intermediate layer comprises a first layer made of electrical insulating material in contact with the connection line and a second layer deposited onto the first layer, said second layer being made of a material such that it is little or not sensitive to a step of releasing the microelectronic and/or nanoelectronic structure. Advantageously the first layer has a planar face whereon is deposited the second layer. The second layer is for example made of Si, silicon nitride, metal (AlSi, AlCu, etc.) or of hafnium oxide ($HfO_2$), etc. This first layer is advantageously planarising.

The channel forms in a very advantageous application a gas chromatography microcolumn.

Another subject-matter also is a method for carrying out at least one device according to the invention, comprising the steps of:

a) carrying out the microelectronic and/or nanoelectronic structure on a substrate and the at least one connection line, b) forming the intermediate layer in such a way that it has a substantially planar free face that has an opening above said at least sensitive portion c) carrying out of a cover substrate, comprising a fluid channel, d) sealing of the cover substrate on the intermediate layer in such a way that the fluid channel is arranged facing the microelectronic and/or nanoelectronic structure.

During the step b), the layer is according to an advantageous mode deposited and then structured to be eliminated above all or a portion of the sensitive portions of the MEMS/NEMS structures.

The step c) can be carried out at any moment of the method as long as this is before the step d).

The method can comprise, after the step b), a step of releasing said microelectronic and/or nanoelectronic structure.

The method for carrying out can further comprise a step of carrying out a functionalisation layer inside the fluid channel on the microelectronic and/or nanoelectronic structure and/or on the walls of the cover and/or on the intermediate layer, said step being carried out before the sealing.

Alternatively, the functionalisation layer can be formed before the release of the sensitive portion, and even before the forming of the sensitive structure.

Functionalisation layers at different locations of the fluid channel can be deposited, in this case, these layers can be of the same nature or not.

In an advantageous example, the step of sealing uses a dry film, this step can comprise the sub-steps of:
  rolling of the dry film on the base faces of the walls of the cover,
  structuring of the dry film
  bringing closer together of the cover and of the substrate comprising the microelectronic and/or nanoelectronic structure,
  applying a pressure in such a way as to crush the dry film.

Heating can also be applied during the application of the pressure.

Surface preparations can be advantageously applied on the interfaces before the sealing by dry film in order to further improve the adherence, the preparation can be a treatment of the plasma type.

The carrying out of the intermediate layer can take place by depositing a first layer of electrical insulating material and by depositing a second layer on the first layer.

The material of the second layer is more preferably chosen as little or not sensitive to the step of releasing the microelectronic and/or nanoelectronic structure, when this method comprises a step of releasing.

According to another embodiment, the sealing is a eutectic sealing or by thermo-compression, or par molecular sealing or by screen printing.

The release can be obtained by etching using hydrofluoric acid vapour.

When several devices are carried out simultaneously, said substrate can comprise several microelectronic and/or nanoelectronic structures and the cover substrate comprising several covers, with the covers being sealed simultaneously on the substrate comprising the microelectronic and/or nanoelectronic structures, in such a way that a fluid channel of a device can communicate or not with the fluid channel of other devices.

When several devices are arranged in a matrix, the fluid channels of devices in lines can communicate together while the fluid channels of devices in columns are arranged next to one another.

When several devices are carried out, the method for carrying out can comprise the steps of:
  carrying out pre-cuts in a direction perpendicular to the fluid channels in the cover substrate and in the substrate bearing the microelectronic and/or nanoelectronic structures,
  carrying out cuts or pre-cuts in a direction parallel to the fluid channels in the substrate bearing the microelectronic and/or nanoelectronic structures,
  separating devices.

These partial or total cuts can be obtained by laser amorphisation or cutting.

The separation of the devices is carried out for example by cleavage.

The cover substrate can comprise cavities formed beforehand between the channels wherein are located contact pads after sealing, the method can further comprise a step of cutting the cover substrate in order to open said cavities. This step can be carried out before or after the cuts or pre-cuts in order to separate the devices.

When a functionalisation layer has been formed on said microelectronic and/or nanoelectronic structure and on the contact pads before sealing, said method can comprise the step of removing by etching the functionalisation layer on the contact pads after sealing and opening cavities in the cover, with said covers forming masks to this etching for the microelectronic and/or nanoelectronic structures.

BRIEF DESCRIPTION OF THE DRAWINGS

This invention shall be better understood using the following description and annexed drawings wherein.

DETAILED DESCRIPTION OF PARTICULAR EMBODIMENTS

In this application, NEMS/MEMS portion means a mechanical structure comprising a fixed structure and at least one sensitive structure and means of actuating and/or of transduction of at least one characteristic of the sensitive structure.

The sensitive structure can be a mechanical suspended structure and comprise means of actuating and/or of transduction of the mechanical movement. Electrical connections are provided in order to connect the mechanical structure to the outside environment. This MEMS/NEMS portion can comprise a network of NEMS and/or MEMS structures, with possibly several levels of metallisation in order to carry out the required interconnections. For the purposes of simplicity, a MEMS or a NEMS will be designated as NEMS.

The expressions "sensitive portion" and "suspended portion" shall be used indifferently keeping in mind that in certain applications of the electromechanical type this sensitive portion is mobile.

The same reference shall be used to designate the elements that have the same functions and substantially the same shape.

Figure 1A:
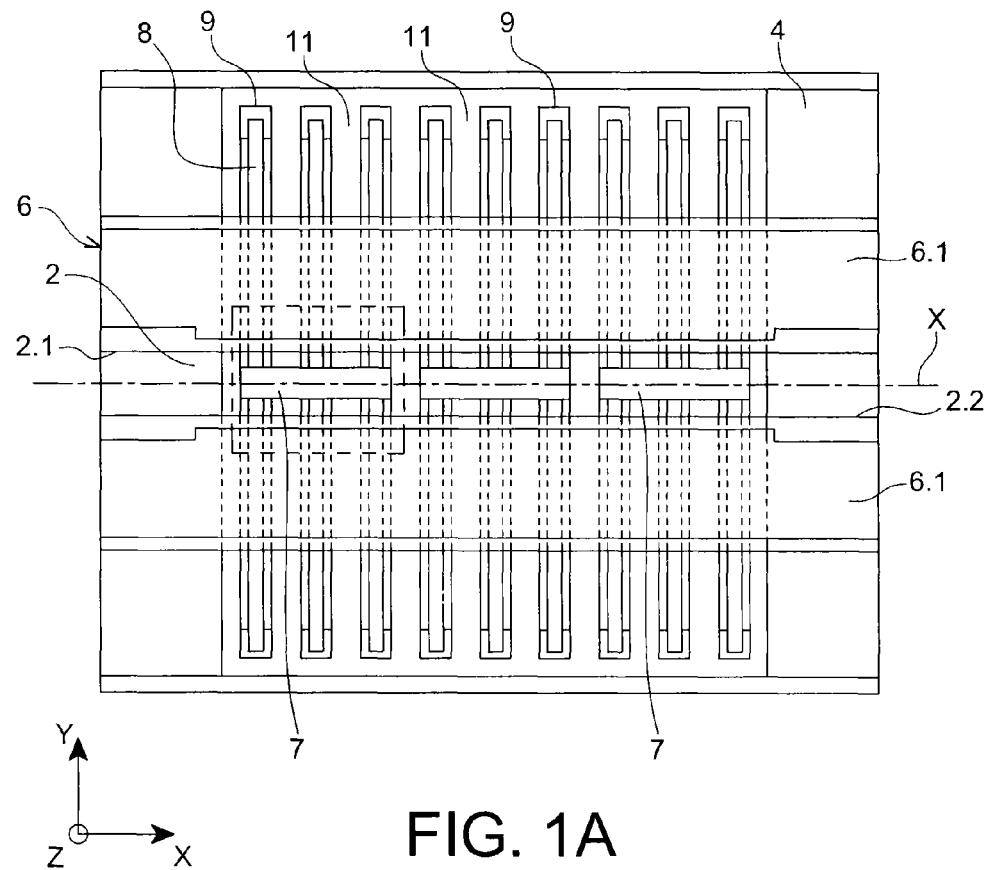
FIG. 1A is a top view of a fluid channel device that integrates MEMS/NEMS structures with an intermediate layer according to a first embodiment.
Figure 1B:
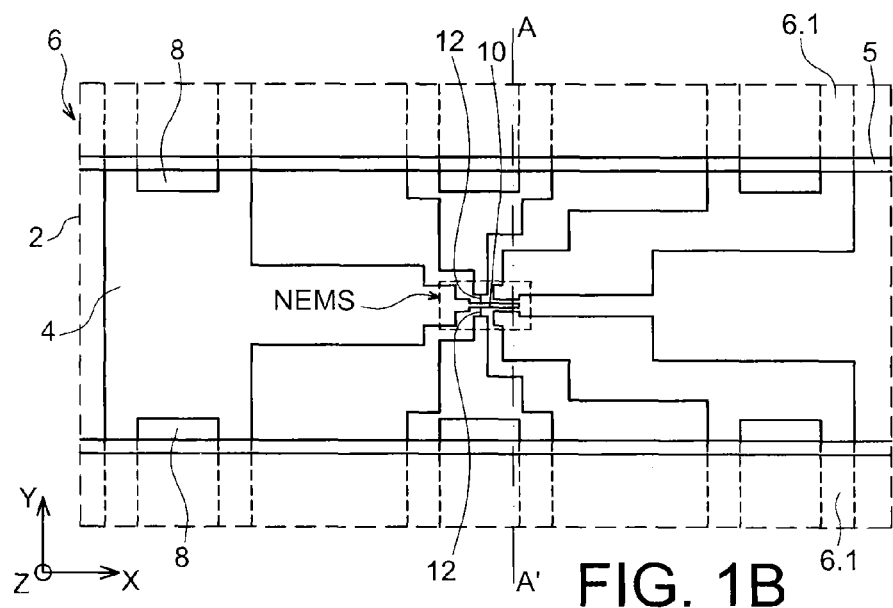
FIG. 1B is an enlarged view of FIG. 1A, FIGS. 2A, 2B, 2B', 2C, 2C' are cross-section views of FIG. 1B according to the plane A-A of different embodiments wherein the sealing is carried out by means of a dry film.

FIGS. 1A and 1B show a diagrammatical top view of a fluid channel device according to a first embodiment, with the top of the cover omitted.

The device comprises a fluid channel 2, which is rectilinear of axis X in the example shown. The fluid channel 2 is delimited by a substrate 4 and a cover 6 added onto the substrate 4. For example, the flow in the fluid channel is carried out from one longitudinal end 2.1 to the other 2.2 of the fluid channel 2.

In the example shown, the cover 6 is formed using a substrate wherein a cavity 5 has been arranged. The cavity 5 delimits with the substrate bearing the NEMS/MEMS structure the fluid channel 2 which provides the circulation and the distribution of a gaseous or liquid mixture. The channel is delimited by two lateral walls 6.1, an upper bottom 6.2 connecting the two lateral walls 6.1 and a lower bottom formed by the substrate 4. The lateral walls 6.1 have base faces that allow for the sealing of the cover on the substrate.

It shall be understood that the inlet end and/or the outlet end of the fluid channel could for example be carried out in the upper bottom 6.2 of the channel or in the substrate 4.

Alternatively, the cover 6 could have a more complex shape, for example the latter could comprise a long channel of optimised shape, for example a spiral, making it possible to carry out a chromatography column that provides the function of separating the compounds of a mixture, with the column integrated a NEMS/MEMS structure.

The substrate comprises a NEMS/MEMS structure 7 located inside the fluid channel 2. In the example shown, the NEMS/MEMS structure comprises three NEMS aligned along the longitudinal axis X.

The device further comprises electrical connection lines 8 extending laterally between the NEMS located in the fluid channel 2 and pads 9 located outside of the fluid channel. The pads 9 are for example directly carried out in the semiconductor material of the NEMS\MEMS structure. They can advantageously be covered with metal in order to provide a good electrical contact. The connection lines 8 can be made of a doped semiconductor of the type of that forming the NEMS/MEMS structure.

The connection lines 8 are separated by trenches 11 in such a way as to electrically insulate the connection lines 8 between them.

These connection lines 8 can be carried out with one or several levels of metal separated by a dielectric material as shall be described in what follows.

These lines can also be carried out in a semi-conductor covered with metal in order to reduce the electrical resistance of the line.

Alternatively, the connection lines can be made of metal, with the contact between the semiconductor wherein is carried out the structure and the metal then being located either in the fluid channel, or outside of this channel, or possibly under the sealing zone separating the fluid channel from the outside. Advantageously, the connection lines 8 comprise a reduced portion made of semiconductor material alone in order to limit the electrical resistances and the parasitic capacities which can degrade the performance of the NEMS components.

More preferably, the metal tracks in order to form the connection lines are carried out preferably in damascene configuration in order to prevent the formation of interstices or voids or zones of a lower density in the filling dielectric and in the material of the intermediate layer, which is able to result in undesirable infiltrations and etchings during the step of releasing mechanical structures, including laterally under the zones of sealing between the substrate and the cover. Furthermore, they could result in lateral leaks outside of the fluid channel.

In the example shown, three pairs of electrical connection lines 8 extending laterally on either side of the fluid channel 2 are provided per NEMS.

A device comprising at least two lateral connection lines extending from the same side in relation to the X axis do not leave the scope of this invention.

FIG. 1B shows an enlarged view of FIG. 1A on an NEMS.

In the example shown, the suspended structure of the NEMS is formed by a beam 10 embedded at one of its longitudinal ends, for example two gauges 12, for example piezoresistive, used to detect the displacement of the beam 10. The ends of the connection lines 8 connected to the NEMS/MEMS structure can be seen.

Figure 2A:
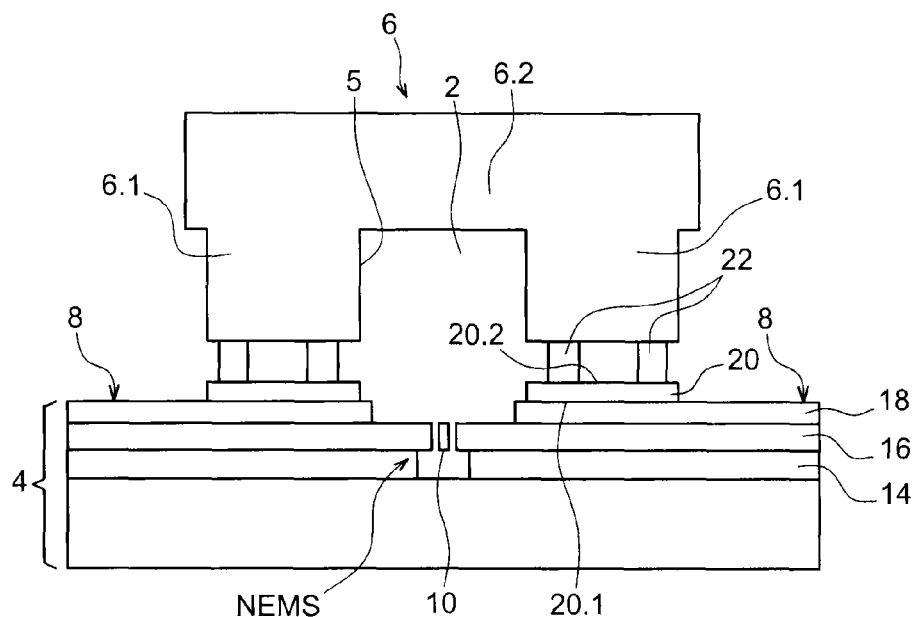

In FIG. 2A, a transversal cross-section view along the plane A-A of FIG. 1B can be seen. This view shows the top of the cover 6.

The substrate 4 comprises a stack of a sacrificial layer 14 used for the carrying out of the NEMS, of a layer 16 as a semi-conductor wherein are carried out the fixed portion and the mobile portion of the NEMS.

In this example, the connection lines 8 are formed both in the layer 16 and from a metal line 18 covering the layer 16.

An intermediate layer 20 covers at least partially the connection lines 8 and a sealing layer 22 is arranged between the intermediate layer 20 and the cover 6.

The intermediate layer 20 is present at least on the sealing interface between the NEMS/MEMS structure 7 and the cover and is absent from the zones of the NEMS/MEMS structure in order to leave the portion or portions of the NEMS/MEMS suspended structure in contact with the medium present in the fluid channel. In the first embodiment shown in FIGS. 1A, 1B, 2A to 2C and 5A to 5C, the intermediate layer 20 is localised only close to the sealing interface between the NEMS/MEMS structure 7 and the cover 6, and more particularly between the connection lines 8 and the cover 6.

The intermediate layer 20 comprises a first face 20.1 in contact with the connection lines 8, with this face 20.1 following the topology of the connection lines 8 and of the substrate 4 and a second face 20.2 in contact with the cover 6. The intermediate layer 20 is such that the second face 20.2 is able to carry out the sealing of the cover 6 comprising the NEMS portion, by providing both the seal along the fluid channel and the passage of the connection lines 8 and this is a simplified manner. The presence of the intermediate layer 20 makes it possible to offset the topology generated by the prior forming of the NEMS/MEMS structure and of the connection lines 8.

As indicated hereinabove, the intermediate layer 20 allows for the passage of at least one portion of the electrical interconnections between the inside of the fluid channel 2 and the outside of the fluid channel 2 while still providing a relatively planar sealing interface that facilitates the obtaining of a seal.

In the example shown, the intermediate layer 20 has electrical insulation properties in such a way as to electrically insulate the connection lines 8 from each other. Furthermore, its material is chosen in such a way as to allow for the obtaining of a face 20.2 that is sufficiently planar for the sealing. According to the type of sealing, the surface state of the face 20.2 obtained directly after the deposit of the intermediate layer can be sufficient, or a step of planarisation is carried out for example a step of chemical-mechanical polishing after the forming of the intermediate layer.

The material of the intermediate layer is chosen as to be etched, for example as anisotropic etching.

More preferably, the material of the intermediate layer 20 is chosen in such a way as to have good selectivity for the etching in relation to the method of releasing mechanical structures and to not generate residue during this step.

The material of the intermediate layer is also chosen in such a way as to be compatible with the materials used for the final assembly of the device between the substrate bearing the NEMS/MEMS structure and the cover.

In the case where a functionalisation layer is implemented, the material of the intermediate layer is chosen to be compatible with that of the functionalisation layer, in particular in such a way as to provide good adherence of the latter.

For example, the material of the intermediate layer is a dielectric material, for example a silicon oxide, such as for example $SiO_2$ or an oxide formed from a silane base or an oxide formed from a tetraethylorthosilicate (TEOS) base, a silicon oxide of the LTO (Low Temperature Oxide) type formed by low pressure chemical vapour deposition (LPCVD) that is not doped or is doped with phosphorus (PSG: phospho-Silicate-Glass) or doped with Boron and Phosphorus (BPSG: Boro-Phospho-Silicate Glass), an oxide deposited via PECVD (Plasma Enhanced Chemical Vapour Deposition).

Very advantageously, the intermediate layer 20 comprises several materials each having properties that intervene in the carrying out of the device. For example, these materials can be arranged in successive layers. For example, the intermediate layer comprises two layers, a first layer deposited onto the connection lines, designated as planarising layer, which makes it possible to fill in the topology of the NEMS/MEMS structure and connection lines while still providing the electrical insulation, and a second layer deposited onto the first layer intended to increase the protection of the whole during the step of releasing the mechanical structure.

The flatness of the planarising layer provides the flatness of the layer. As such, a larger degree of liberty is allowed for the choice of the material for the planarising layer. By way of example, the material of the first layer is made of silicon oxide and the material of the second layer is made of amorphous silicon or of any other material that can resist the release via hydrofluoric acid in the case where the sacrificial layer is made of silicon oxide, such as a metal, a silicon nitride, etc. which makes it possible to protect the upper surface of the first layer made of oxide during the release.

This embodiment with at least one planarising layer and a protective layer is particularly interesting, as the etching speeds of the silicon oxides forming the planarising layer are in general much greater, for example at least 10 times greater, than the etching speed of the oxide layer of an SOI substrate for example which is carried out during the release of the mobile structure or structures. In the absence of such a protective layer, the release etching of the mobile structure or structures could cause a substantial consumption of the planarising layer. This embodiment with two layers therefore advantageously makes it possible to reduce the thickness of the planarising layer. For example, its thickness can be a few tens of nm.

In the embodiment wherein the intermediate layer comprises only a single material its thickness is determined in order to take into account of the consumption of material during the release etching. In this case, the thickness of the intermediate layer is for example of a magnitude of a few µm.

Figure 2B:
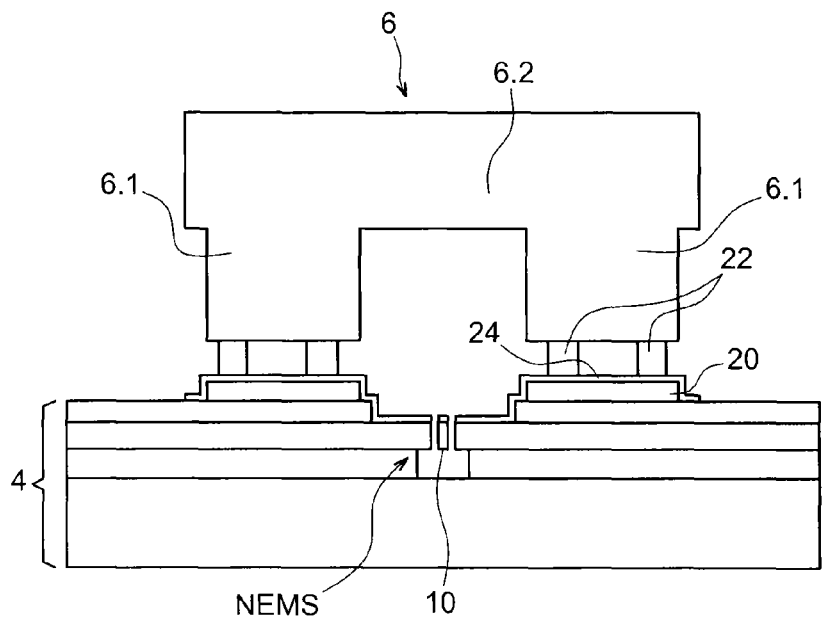
Figure 2B:
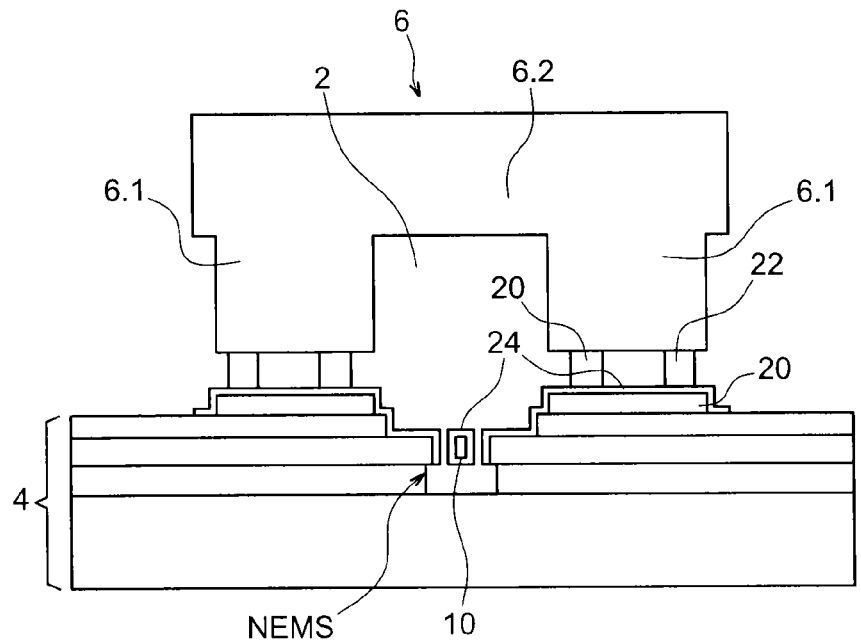
Figure 2C:
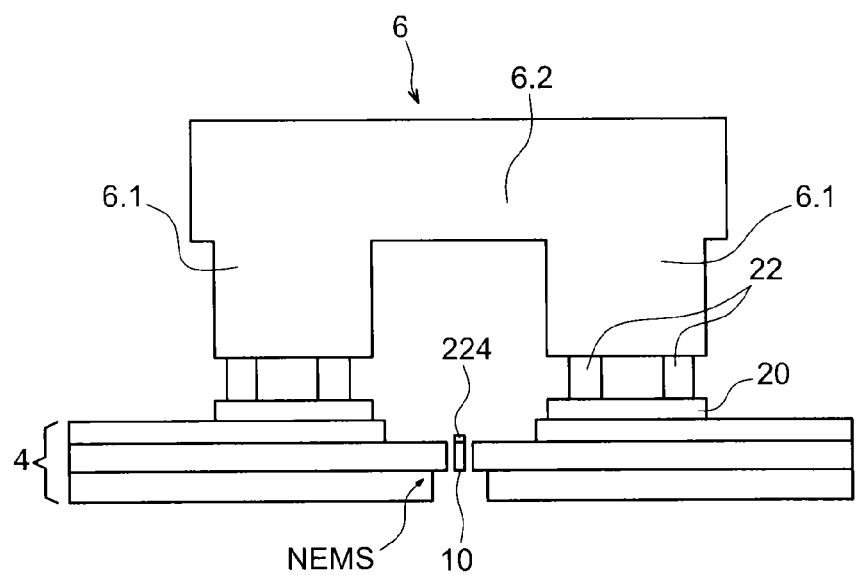
Figure 2C:
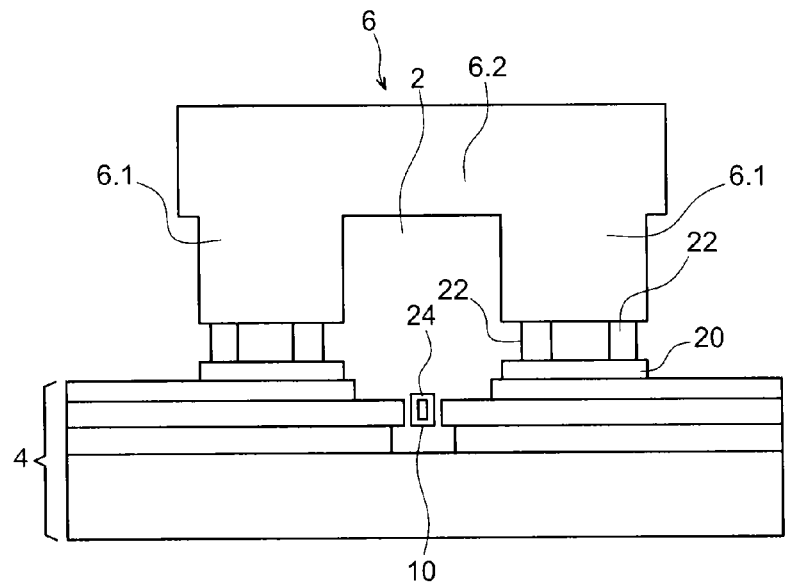

In the example of FIGS. 2A to 2C and particularly advantageously, the sealing is carried out by means of a dry resin film 22 or DFR (Dry Film Resist).

For example, a thin resin film 22 is applied by rolling on the lower face of the cover 6 intended to come into contact with the intermediate layer 20 and is structured by photolithography. The cover and resin film unit, is added and sealed on the intermediate layer 20.

In the example shown in the FIGS. 2A to 2C, the thin film 22 has the form of two parallel beads, substantially having the same sealing surface. These beads are obtained after insulation and development of the dry film.

The dry film is for example a resin with epoxy, phenol, acrylic or silicone bases for example.

The dry film has for example a thickness between a few µm to several tens of µm, and even a few hundreds of µm with a multilayer of dry film, advantageously a few µm only in order to prevent interaction between the material of this sealing bead with the medium propagating in the fluid channel.

The sealing by means of a dry film has the following advantages:
  this sealing can take place at a relatively low temperature, generally below 250° C. and even at ambient temperature, which is compatible with the existence of metal tracks. Indeed, in the case of aluminium tracks, the maximum temperature is about 400° C.
  this sealing is compatible with a large number of materials,
  the dry film can be carried out on the cover despite the strong topology due to the fluid channel already formed, which makes it possible to not carry out operations of the photolithography type on the NEMS/MEMS structure as the latter already contains released mechanical structures,
  this sealing by dry film has the advantage of being less demanding in terms of the required surface state (flatness, roughness, presence of particles) at the sealing interface than sealings of the molecular or eutectic type or even by thermo-compression. As such, the implementing of a dry film can allow for the sealing without carrying out prior mechanical-chemical polishing of the planar face 20.2 of the intermediate layer, with its surface state directly after deposit able to be sufficient.

This characteristic makes it advantageously possible to carry out this sealing in the presence of a functionalisation layer at the NEMS/Cover sealing interface as is shown in FIG. 2B.

This type of film furthermore offers the possibility of working with substantial thicknesses, for example of a magnitude of several hundreds of µm but also thickness of a few 10 µm; and even a few µm.

In addition, this type of film has good thermal stability.

A sealing via another technique does not leave the scope of this invention, for example this could be a molecular sealing, a eutectic sealing, a sealing or by thermo-compression, or a sealing by screen printing, or by glass frit etc. However, implementing these techniques can be more complex than sealing by dry film. Indeed, it is preferred to limit the temperatures used in order to not deteriorate the metal tracks already present and possibly the functionalisation layer. Moreover, these temperatures shall be chosen as less than about 400° C. so as to at least preserve the metal layers of the connection lines. They will even be less in order to preserve certain functionalisation layers for example of the polymer type.

In the case where the deposit of a layer is required for the sealing, the latter able to be possibly structured on a single one of the two portions, which is the case for a eutectic sealing, this deposit and this possible structuring are carried out more preferably on the cover. For example for a Au—Si eutectic, a layer of Au is deposited more preferably on the cover.

In the case where the deposit of a layer on each of the two portions is required, for example for a sealing or by thermo-compression, the deposit on the NEMS/MEMS structure is carried out before the release of the structure. The material of this layer is then chosen to be compatible with the method of releasing the NEMS/MEMS structure in such a way that it is not etched during this technological step that intervenes just before the sealing. A layer of Au will then for example be used on the cover and on the intermediate layer for a Au—Au sealing, in the case of a releasing of the NEMS with the hydrofluoric acid in vapour phase.

In FIG. 2B, the device comprises a functionalisation layer 24 covering the intermediate layer 20 and the entire NEMS/MEMS structure. This functionalisation layer 24 is referred to as non-localised. In FIG. 2B', the functionalisation layer surrounds the NEMS structure.

"Functionalisation layer" means a layer present on the surface of the mechanical structure in order to provide it with particular properties. For example in the case of a gas sensor, the functionalisation layer makes it possible to increase the adsorption of gaseous species in a possibly selective manner or, in the case of a biological sensor, the functionalisation layer makes it possible to provide for the grafting of biological species. The functionalisation layer 24 is for example formed from one or from several organic or inorganic materials, polymers, oxides, carbon compounds, semiconductors or other porous materials, etc.

The invention makes it very advantageously possible to carry out the step of depositing the functionalisation layer on an already released mechanical structure, which makes it possible to encapsulate almost entirely the mechanical structure with the functionalisation layer (FIG. 2B') when the deposit of the latter is sufficiently compliant. The functionalisation layer then has a surface of interaction with the surrounding environment that is increased which further increases the interest of a functionalisation layer. The invention allows for the implementing of functionalisation layers on NEMS released by contactless and collective techniques, for example by CVD, LPCVD, PECVD, ALD, epitaxy, porosification, etc. and to then continue with the closing of the component by adding a cover comprising a cavity in such a way as to form the fluid channel. As such, the risks of gluing by deposit of the functionalisation layer by deposit in liquid phase are avoided.

More preferably, the sealing is carried out by means of a dry film 22 as described hereinabove, indeed the temperature of such a sealing is compatible with the presence of a functionalisation layer deposited or formed itself at low temperature, for example made of polymer, etc.

As has been described hereinabove, the sealing par dry film has the advantage of being less demanding in terms of a required surface state (flatness, roughness, presence of particles) at the sealing interface than sealings of the molecular or eutectic type or even by thermo-compression. As such it allows for a sealing even in the presence of a functionalisation layer with the sealing interface between the intermediate layer and the cover.

Furthermore, as this sealing is compatible with a large number of materials, a large degree of freedom is offered in terms of the choice of the functionalisation layer or layers that can be implemented. It can then be considered to implement functionalisation layers of different natures and/or thicknesses on the NEMS and cover portions. This is particularly interesting in the case where the cover forms a gas chromatography column. In this case the cover can receive a functionalisation able to fulfil the function of separating analytes of the mixture to be analysed while the NEMS can receive another functionalisation able to optimise its performance in terms of detection.

FIG. 2C shows another embodiment wherein the functionalisation layer 224 is carried out solely on the suspended portion of the NEMS, the functionalisation layer is then designated as a localised layer. In this example, the functionalisation layer is not present on the sealing zone. In FIG. 2C', the functionalisation layer 224 surrounds the NEMS structure.

Figure 5A:
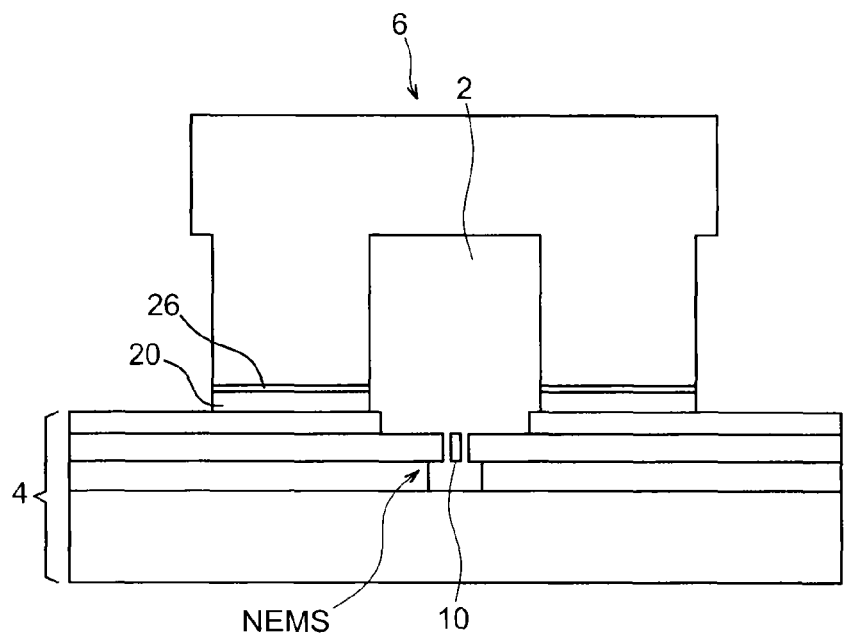
FIGS. 5A to 5C are transversal cross-section views of a fluid channel device according to the first embodiment, having other types of sealing and with or without a functionalisation layer at the MEMS/NEMS portion.
Figure 5B:
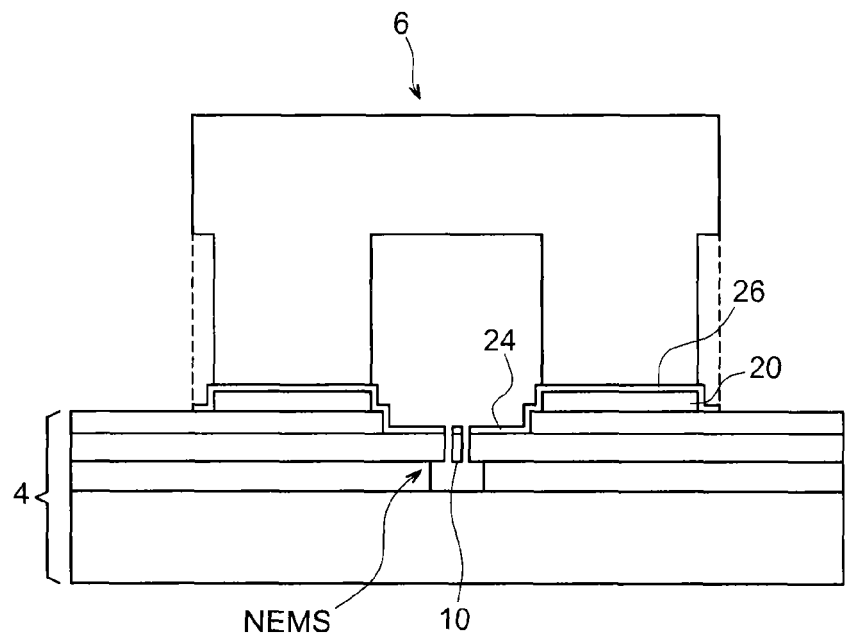
Figure 5C:
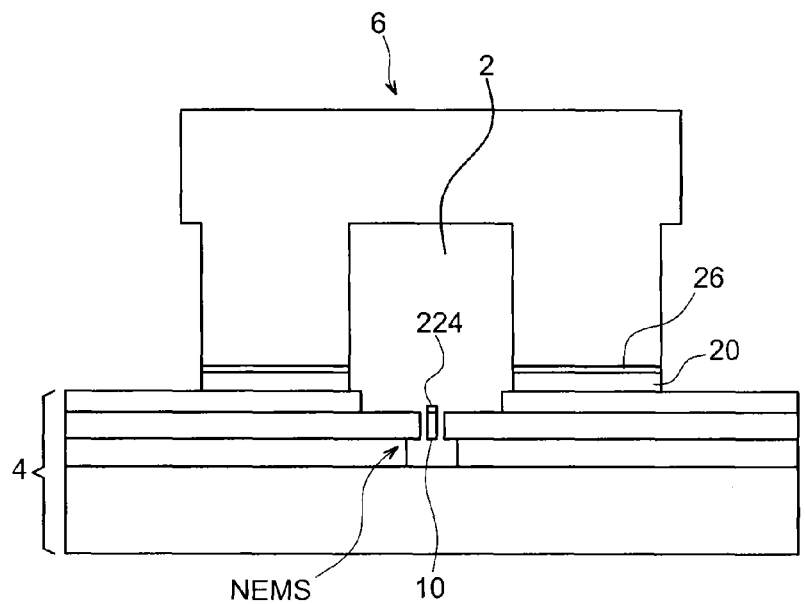

FIGS. 5A to 5C show different examples of the device according to the first embodiment in the case of a sealing other than by dry film. It shall be understood that these examples of sealing also apply to the other embodiments that shall be described hereinbelow. In this example the means of sealing are symbolised by a sealing interface 26.

In the case of a molecular sealing or of an anode sealing, for example in the case where the cover is made of glass, the sealing interface 26 is formed by the face of the cover and the face of the substrate to be sealed.

No adding of material is required. The faces to come into contact are prepared in a manner known to those skilled in the art, for example by chemical-mechanical polishing (CMP), i.e. the face 20.2 of the intermediate layer and the lower face of the cover 6.

A molecular sealing in the presence of a functionalisation layer on the interface, with the functionalisation layer being deposited after the release, can also be considered.

In other methods of sealing, the sealing interface is formed of a layer of one or several materials, this can be a layer of Au—Si, AlGe or AuGe, etc. for example in the case of a eutectic sealing, Au—Au, AuSn, etc. for example in the case of a sealing or by thermo-compression or adhesives in the case of a sealing by screen printing.

In FIG. 5A, the sealing is carried out by a sealing interface 26 between the intermediate layer 20 and the cover 6, with the device not comprising a functionalisation layer.

In FIG. 5B, the device comprises a non-localised functionalisation layer, the sealing is obtained by means of a sealing interface 26 between the functionalisation layer 24 and the cover 6.

In FIG. 5C, the device comprises a localised functionalisation layer 224 on the suspended portion 10, the sealing is obtained by means of a sealing interface between the intermediate layer 20 and the cover 6.

Figure 3A:
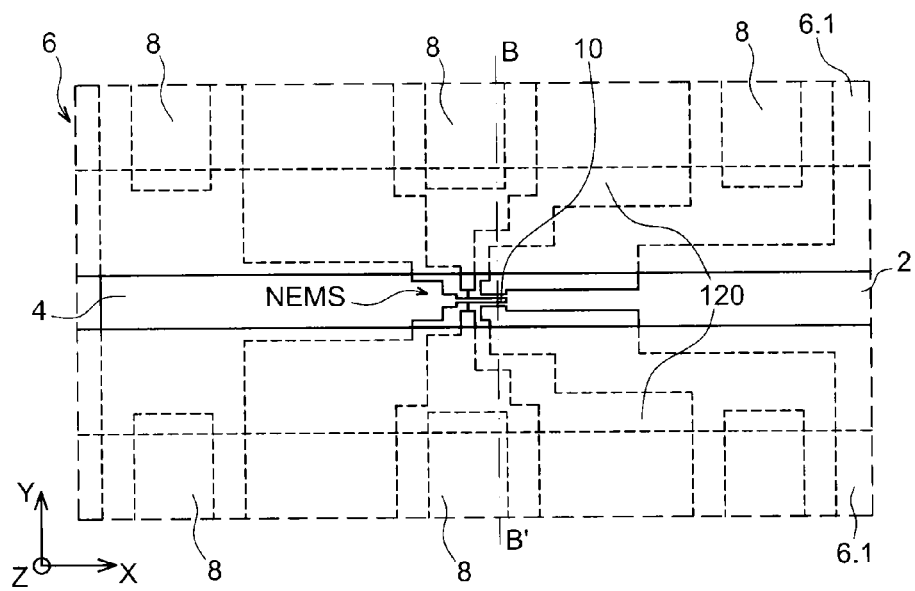
FIG. 3A is a top view of a fluid channel device according to another embodiment wherein the intermediate layer partially covers the MEMS/NEMS structure inside the channel, delimiting a channel parallel to the fluid channel.
Figure 3B:
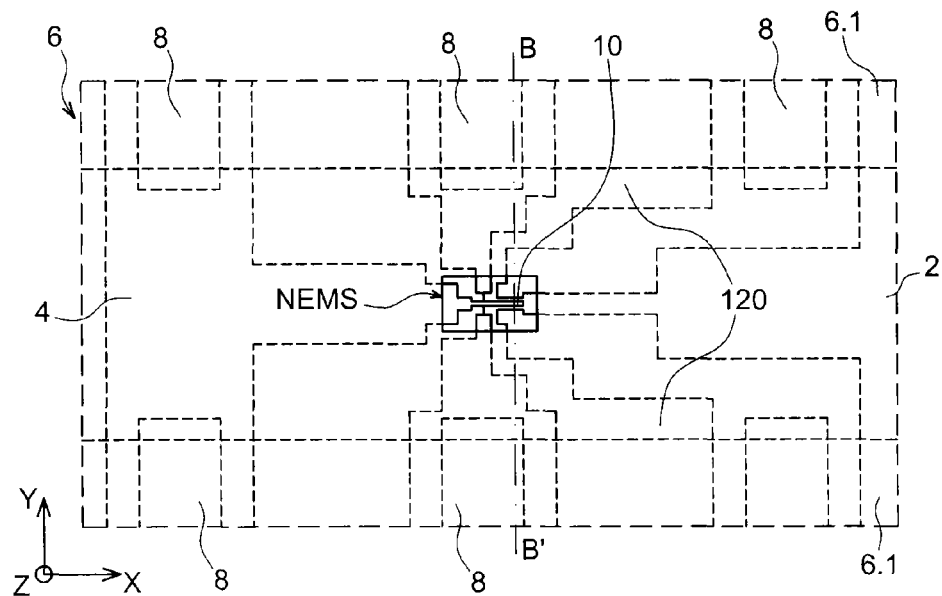
FIG. 3B is a top view of a fluid channel device wherein the intermediate layer partially covers the MEMS/NEMS structure inside the channel, delimiting a window on the sensitive portion.
Figure 3C:
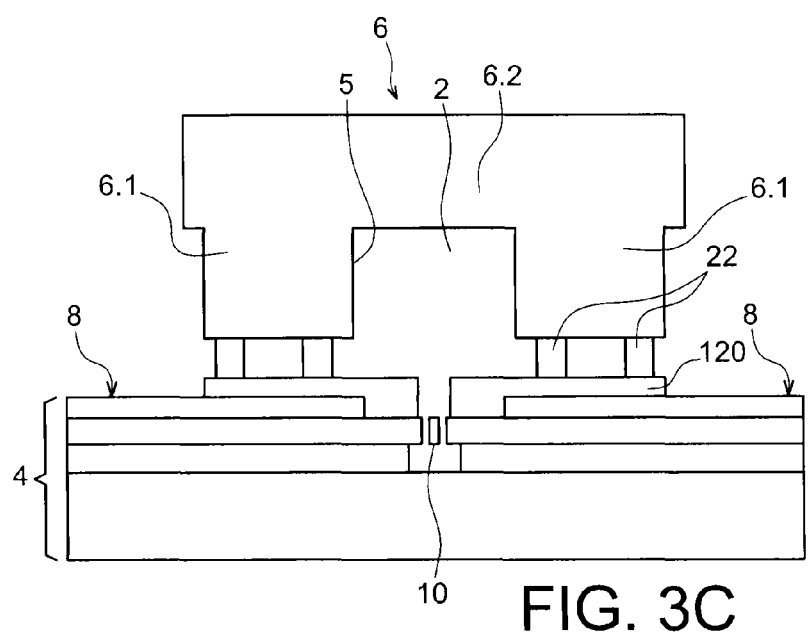
FIG. 3C is a cross-section view of FIG. 3A or of FIG. 3B according to the plane B-B.

In the FIGS. 3A and 3B and 3C, another embodiment is shown of a fluid channel device according to the invention wherein the intermediate layer 120 covers both the connection lines on the sealing zone and the inside of the fluid channel encapsulating as such the NEMS/NEMS structure except the portion of this structure intended to be in contact with the surrounding environment, i.e. generally the suspended portion 10. In the device of FIG. 3A, the intermediate layer 120 is brought as close as possible to the sensitive portions of the MEMS/NEMS structures and as such forms a channel substantially parallel to the fluid channel. In the device of FIG. 3B, the intermediate layer 120 fully covers the MEMS/NEMS structures except for the sensitive portions and as such forms simply an opening above sensitive portions. The intermediate layer 120 encapsulates the connection lines 8 between the various NEMS of the network located in the fluid channel 2. This encapsulation has the advantage of insulating the materials at play on the NEMS portion that, due to their presence in the fluid channel 2, could interact with the medium in circulation in the channel. This is the case for example with metals or dielectrics which are in general implemented in the fluid channel if the mechanical structure is constituted of a dense NEMS network.

A fluid channel device wherein the intermediate layer would not fully cover the portion of the NEMS/MEMS structure that is not intended to come into contact with the surrounding environment does not leave the scope of this invention.

FIG. 3C shows a cross-section view of the device of FIG. 3A or of FIG. 3B along the plane B-B'. The sealing of the cover 6 on the substrate 4 is obtained by the intermediary of a dry film 22 on the intermediate layer 120.

Figure 4A:
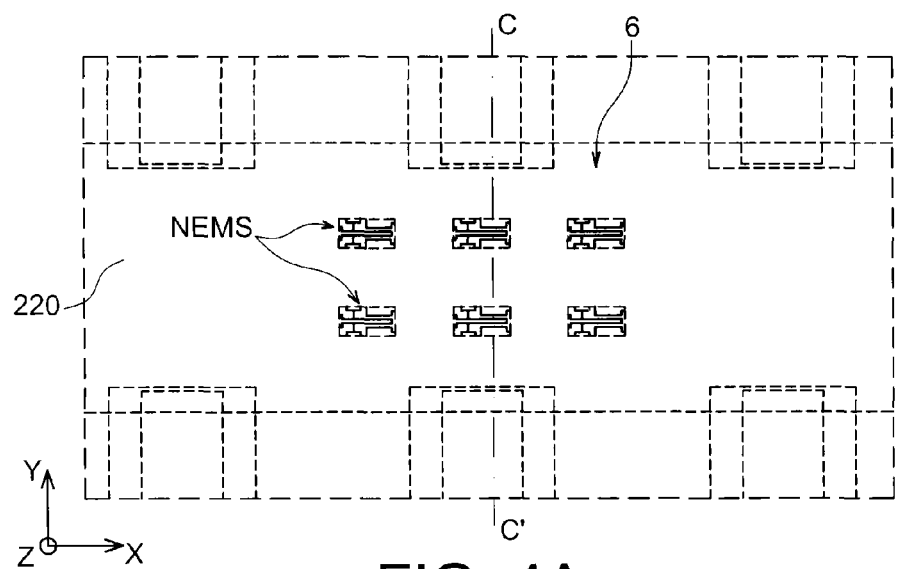
FIG. 4A is a top view of an alternative of the device of FIG. 3A.
Figure 4B:
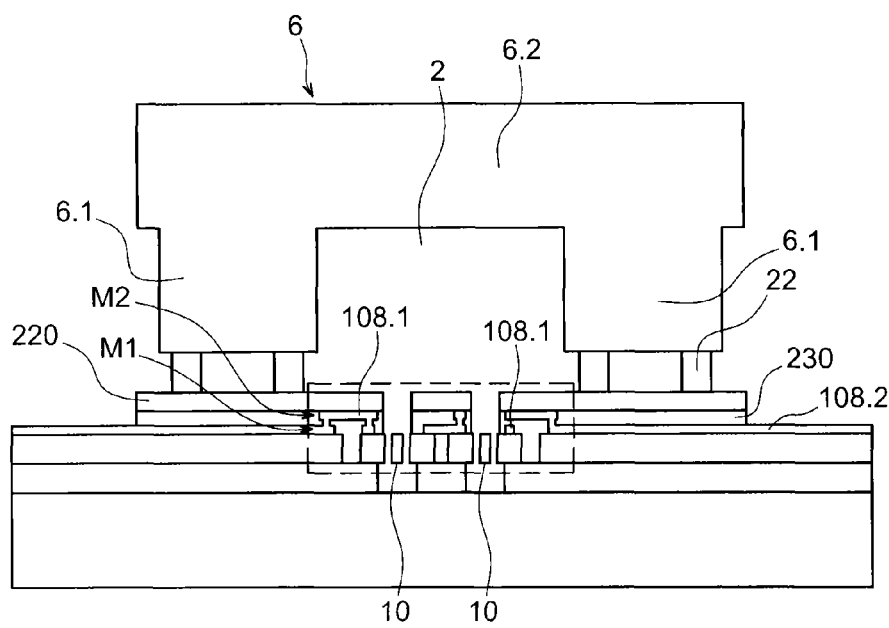
FIG. 4B is a cross-section view of FIG. 4A according to the plane C-C.

This encapsulation via the intermediate layer is particularly interesting to implement in the case of NEMS networks which are connected together by metal or semiconductor conductive paths with possibly several levels of interconnections, with the electrical insulation between the levels being provided by layers of dielectrics, and with the whole being localised in the fluid channel. This embodiment is shown in FIGS. 4A and 4B, with two levels of metal for the interconnections between NEMS located in the fluid channel and a level of metal for the electrical connection with the outside of the fluid channel.

This device comprising several NEMS arranged laterally in the duct. In the example of FIG. 4A, three pairs of NEMS are aligned along the X axis. Interconnection lines 108.1 are then carried out over several layers of metal, two in the example shown, in order to connect between them the NEMS/MEMS structures that constitute the network of NEMS, which is located inside the fluid channel. Interconnection lines 108.2 are also carried out (with a single level in the example shown) in order to connect the network of NEMS with the outside of the fluid channel. These lines are not shown in FIG. 4A but are shown in FIG. 4B. In FIG. 4B, two suspended portions are diagrammed, which correspond to a section CC' of the structure shown in FIG. 4A. The different levels of metallisation are partially encapsulated in an electric insulation layer 230 for example made of oxide. Preferably, the interconnections 108.1 between the NEMS comprise two levels of metal and the interconnections 108.2 in order to connect the network of NEMS outside the fluid channel comprises a level of metal.

Interconnections 108.1 and 108.2 with one or more than two levels of metal do not leave the scope of this invention. This device comprises an intermediate layer 220 deposited onto the interconnection lines 108.1 and 108.2 other than the portions 10 intended to interact with the surrounding environment.

An example of the method for carrying out devices with a fluid channel according to this invention shall now be described.

The method which shall be described allows for the collective carrying out of several devices simultaneously, with the latter then being separated at the end of the method of manufacture. But it shall be understood that the method applies to the carrying out of a single fluid channel device.

In a first phase, the substrate provided with the NEMS/MEMS structure is carried out using a silicon substrate on an insulator (SOI, or Silicon-on-Insulator) for example. Alternatively, any substrate can be used that comprises a layer wherein would be carried out the NEMS/MEMS structure, with this layer being formed on a sacrificial layer allowing via its etching a release of the NEMS/MEMS structure. The material of the layer wherein is carried out the NEMS/MEMS structure can be a single crystal or polycrystalline semiconductor for example Si, Ge, SiGe, SiC, GAAs, InAs, InP, etc. The sacrificial layer can be present over the entire substrate or be localised only at certain locations where the NEMS will be carried out.

It can be considered that the NEMS/MEMS structure comprises an optical function in such a way as to include MOEMS (Micro-Opto-Electro-Mechanical Systems) and/or integrate an integrated electronic portion, CMOS, etc.

The substrate SOI comprises a layer of insulation material 28, for example of silicon oxide and a layer of silicon 30.

During a first step, the silicon of the layer 30 is doped.

Figure 6A:
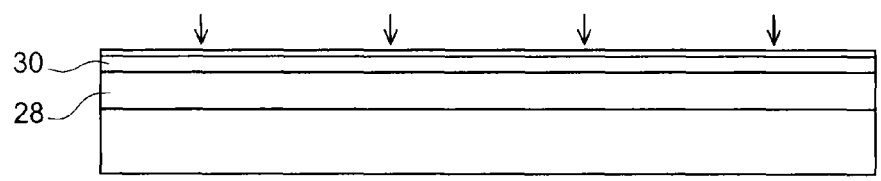
FIGS. 6A to 6L are diagrammatical views of a method of carrying out a substrate provided with at least one MEMS or NEMS structure for the carrying out of a fluid channel device according to the invention.

The element obtained as such is shown in FIG. 6A.

During a following step, the NEMS structures and the semiconductor interconnection lines are carried out.

A photolithography and then an anisotropic etching of the layer of silicon 30 are carried out in a known manner.

Then takes place a step of stripping on the silicon and on the layer of oxide 28 in order to remove the layer of photosensitive resin.

Figure 6B:
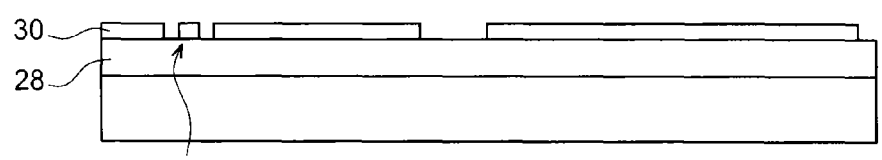

The element obtained as such is shown in FIG. 6B. In FIG. 6B which is a cross-section view a single NEMS can be seen but more preferably the structure comprises a plurality of NEMS in the direction X. The structure can also comprise several NEMS in the direction Y.

During the following steps, the connection lines made of metal are carried out. For this, a deposit of a dielectric layer 32 on the structured layer 30 then takes place, this is for example oxide formed from a silane $SiH_4$ base of which the thickness is greater than the topology of the layer of structured silicon 30.

Figure 6C:
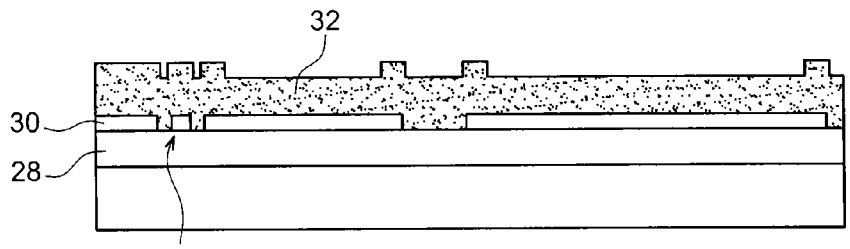

The element obtained as such is shown in FIG. 6C.

A step of chemical-mechanical polishing or CMP is then carried out in order to make the surface of the layer 32 flat. More preferably, beforehand a photolithography of the "countermask" type and a partial etching of the layer 30 of the height of the topology to be recovered are carried out, which facilitates the step of polishing and makes it possible to reduce its duration.

Figure 6D:
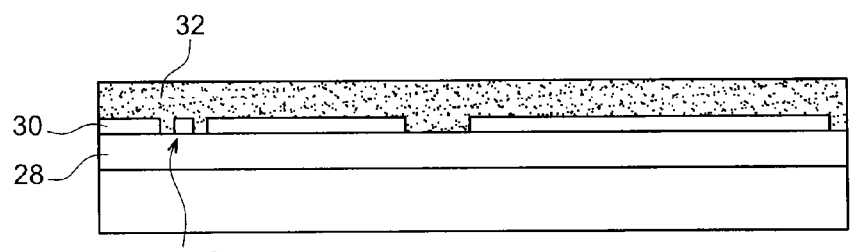

The element obtained as such is shown in FIG. 6D.

During a following step, the layer 32 is opened by photolithography in order to reach the layer of silicon 30 and prepare the carrying out of electrical contacts.

Figure 6E:
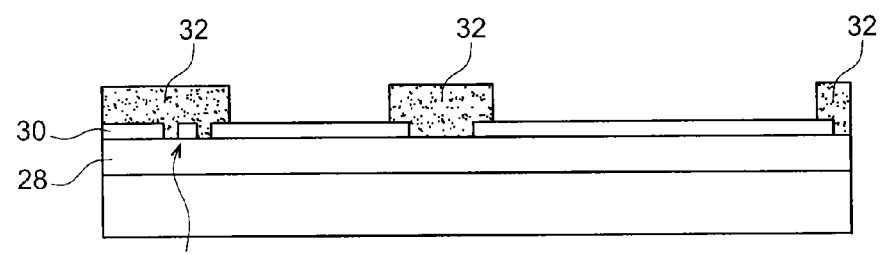

The element obtained as such is shown in FIG. 6E.

During a following step, a layer of metal 34 is deposited for example of AlSi, with the latter having the advantage of offering good resistance to the etching by hydrofluoric acid vapour which takes place in order to release the mechanical structures.

Figure 6F:
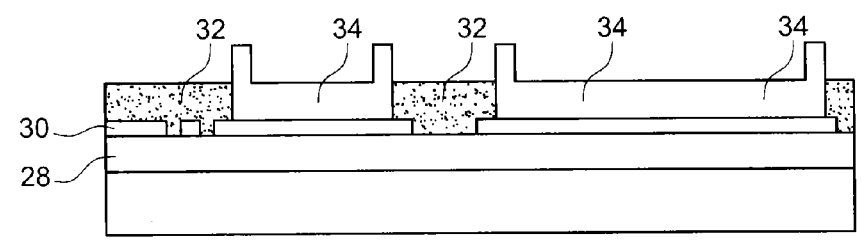

During a following step, the metal layer 34 is etched (FIG. 6F).

During a following step, chemical-mechanical polishing takes place.

Figure 6G:
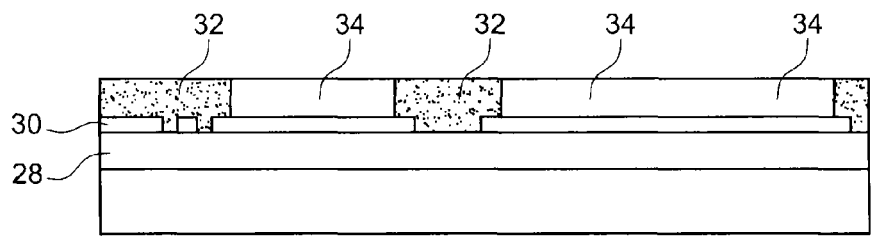

The element obtained as such is represented in FIG. 6G.

The following steps describe the carrying out of the intermediate layer 20.

In the example shown, the intermediate layer 20 comprises two layers. A layer of dielectric material 35 forming the planarising layer is deposited. The planarising layer is for example an oxide formed with a silane $SiH_4$ base, or of an oxide formed from a tetraethylorthosilicate (TEOS) base. A protective layer 36, for example made of amorphous Si, silicon nitride, metal (AlSi, AlCu, etc.), hafnium oxide ($HfO2$), is then deposited onto the layer 35, with the latter increasing the resistance to the etching with hydrofluoric acid vapour.

In the case of an intermediate layer of a single material, its thickness is determined in such a way that it is able to protect in particular the connection lines during the final step of releasing mechanical structures, i.e. its thickness is selected in such a way that it is sufficient to take into account its decrease due to the release etching so that it still covers the connection lines. As mentioned hereinabove, the thickness of the intermediate layer in this case can be for example of a magnitude of a few µm.

Due to the CMPs carried out beforehand and in particular the CMP carried out beforehand on the layer 34, the surface state of the intermediate layer allows for a sealing by dry film without having recourse to a later polishing. A step of polishing can be carried out, in particular in the case of a molecular sealing.

Figure 6H:
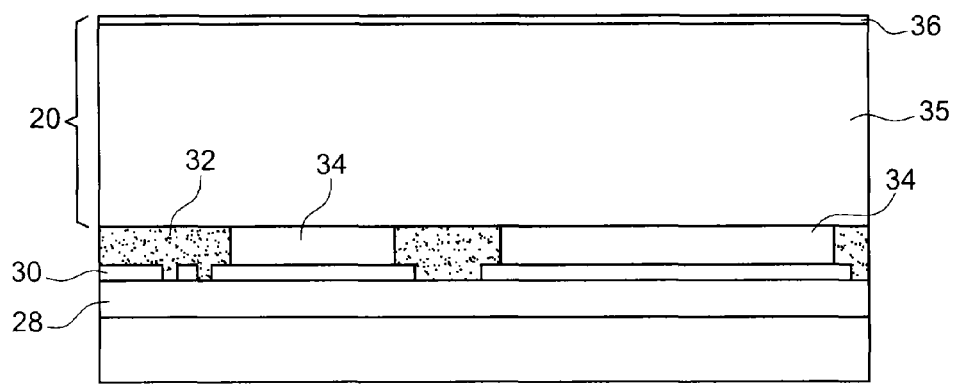

The element obtained as such is shown in FIG. 6H.

During a following step, the intermediate layer is etched in such a way as to reach the NEMS/MEMS structure to be released. For example an etching plasma with a $SF_6$ base can be used for the layer of amorphous Si and an etching plasma with a $CHF_3$ base for the etching of the silicon oxide forming the intermediate layer.

Figure 6I:
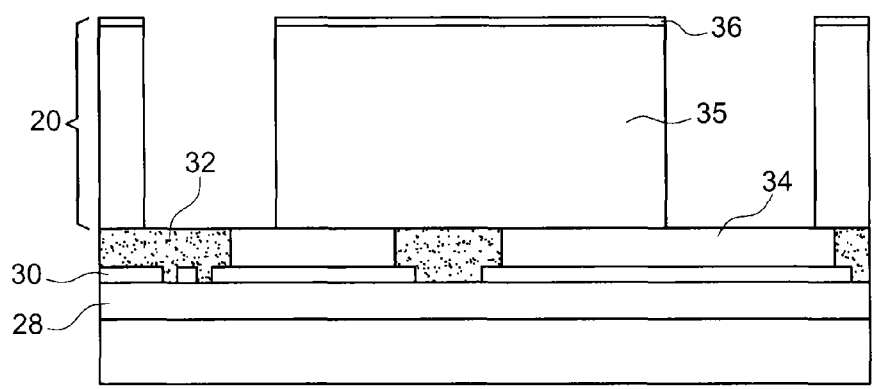

The etching of the intermediate layer 20 is adapted in order to preserve both the metal interconnections and the NEMS/MEMS structure of semiconductor material. As such, the shape of the openings is determined for example via photolithogravure in such a way as to take into account the length of the release of the mechanical structures that intervene at the end of the "NEMS" method, as this step can provoke an undesired lateral etching of the planarising layer of the intermediate layer 20, which, if were not controlled, could result in clearing undesired zones such as metal interconnections, zones under the sealing interface with the cover. In addition, the etching of the opening in the intermediate layer is more preferably stopped on the metal layer above the semiconductor, before reaching the semiconductor, so as to not damage the semiconductor layer that constitutes the mechanical structure. In FIG. 6I, the stopping of the etching above the structure can be seen.

The element obtained as such is shown in FIG. 6I.

During a following step, the NEMS/MEMS structure, in particular the mobile portion or portions are released. The release takes place for example by isotropic etching by means of hydrofluoric acid vapour of the dielectric materials surrounding the NEMS structure, this is layers 28 and 32. The layer 28 can be etched entirely or partially. Due to the presence of the protective layer 36, the layer 35 is protected, its thickness does not decrease. On the other hand the lateral etching of the planarising layer 35 is diagrammed, the layer 36 not being etched.

Figure 6J:
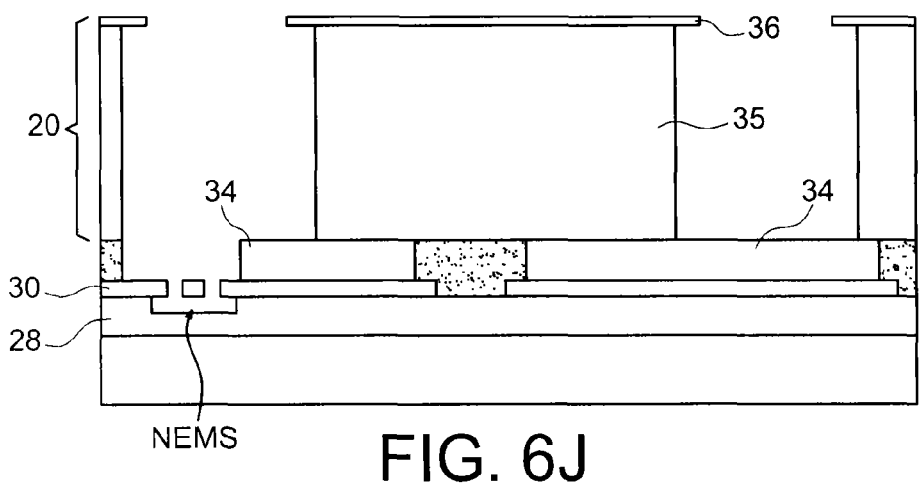

The element obtained as such is shown in FIG. 6J.

Figure 6K:
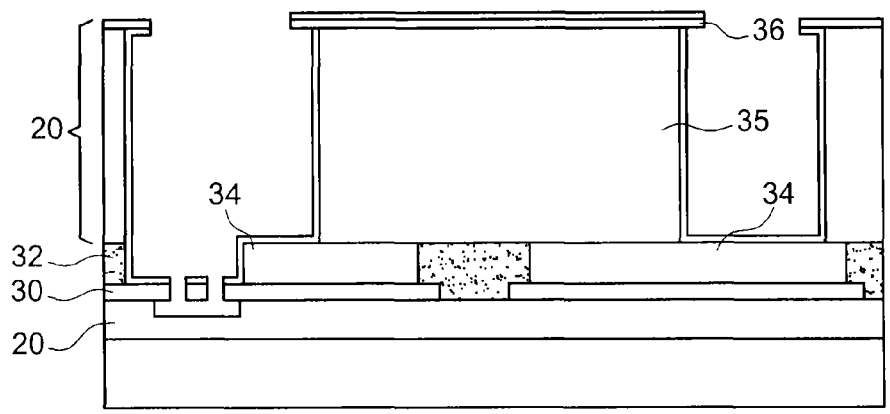

FIG. 6K shows the element of FIG. 6J comprising a non-localised functionalisation layer on the suspended portion of the NEMS. This here entails showing the carrying out of a structure of the type of that shown in FIG. 2B.

Figure 6L:
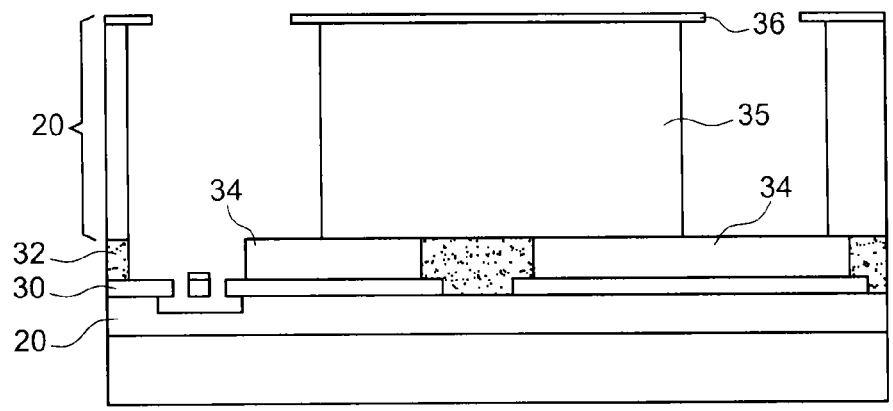

FIG. 6L shows the element of FIG. 6J comprising a functionalisation layer localised on the suspended portion of the NEMS. This here entails showing the carrying out of the structure shown in FIG. 2C.

These functionalisation layers can be carried out in different ways by gas or liquid phase deposits. Preferably, gas deposit techniques for example by CVD (Chemical Vapour Deposition), by LPCVD, by PECVD, by ALD (Atomic Layer Deposition), etc. are used. Epitaxy and/or porosification techniques of materials and/or of the evaporation type can also be implemented. These techniques are preferred to techniques by liquid means, of the spray or spotting (depositing of drops) type, because they make it possible to avoid implementing liquid phases in the presence of released NEMS structures. However, these techniques can also be used, for example if the NEMS/MEMS structures are sufficiently rigid.

The deposited materials forming the functionalisation layer or layers can be for example materials of the polymer, dielectrics, semiconductors type or other porous materials, metals, etc.

In the case of a localised deposit, mechanical masking techniques (stencil), lift-off techniques known in the methods of carrying out microsystems, or even techniques of spotting consisting in depositing drops of liquid solution locally, etc. can be used.

In FIG. 6K, the functionalisation layer is shown only on the surface of the NEMS. Preferably, the functionalisation layer surrounds the NEMS, with the thickness of the functionalisation layer being not necessarily uniform all around the mechanical structure. This deposit is obtained by implementing compliant deposition techniques, for example by CVD.

An example of the steps of carrying out the cover 6 shall now be described using a substrate 38 polished on its two faces, for example made of silicon, glass, quartz, etc., designated as cover substrate 38.

Firstly, marks (not shown) are defined and then etched on the rear face 38.1 and on the front face 38.2 of the substrate, with these marks used for the alignment between the substrate NEMS and the cover during their sealing.

Figure 7A:
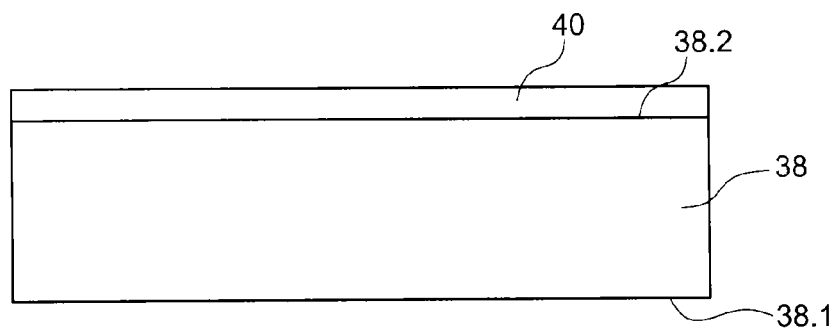
FIGS. 7A to 7C are diagrammatical views of a method for carrying out a cover for the carrying out of a fluid channel device according to the invention, FIG. 8 diagrammatically shows the step of assembling the cover of FIG. 7C and of the substrate of FIG. 6K, FIGS. 9A to 9C diagrammatically show the various steps intended for the separation of the devices with fluid channels in the case of a method for the collective carrying out of devices.

During a following step, a deposit of a hard mask, for example of a mask of silicon oxide of a few µm thick, is carried out on the front face 38.2 of the substrate 38 (FIG. 7A). A photolithography and an etching of the mask 40 are carried out in order to define the cavities.

Then, the cover substrate 38 is etched for example by deep reactive ionic etching (DRIE) with for example a method of the "Bosch" type consisting in a succession of steps of etching with a plasma $SF_6$ and passivation with a plasma $C_4F_8$ as such forming the cavities that will delimit the fluid channels. The depth of the etching is for example of a magnitude of a few hundreds of µm. This etching also advantageously makes it possible to carry out cavities (not shown) intended to be positioned above electric pads after assembly with the substrate of the NEMS/MEMS structure, this in the particular case where several devices are carried out collectively, with these cavities allowing for the separation of the devices, as shall be described hereinbelow.

The hard mask can then be removed for example by wet etching of the HF type.

Figure 7B:
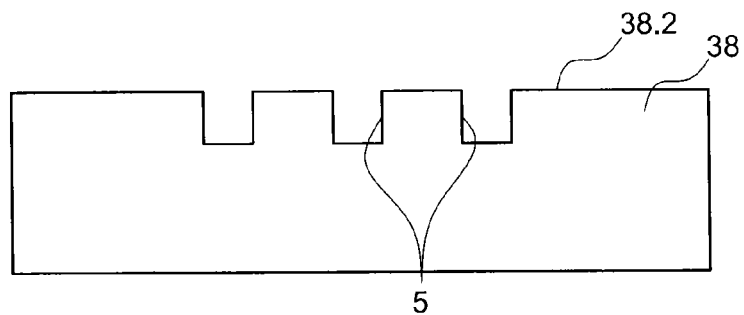

The element obtained as such is shown in FIG. 7B and comprises a plurality of covers 6.

During a following step, the cover substrate 38 is prepared for a sealing on the NEMS/MEMS structure by means of a dry film.

The dry film 42 is then fastened onto the front face 38.2 of the cover substrate 38, this fastening is advantageously obtained by rolling. This rolling makes it possible to work despite the strong topology due to the existence of the fluid channels on this side of the substrate.

Figure 7C:
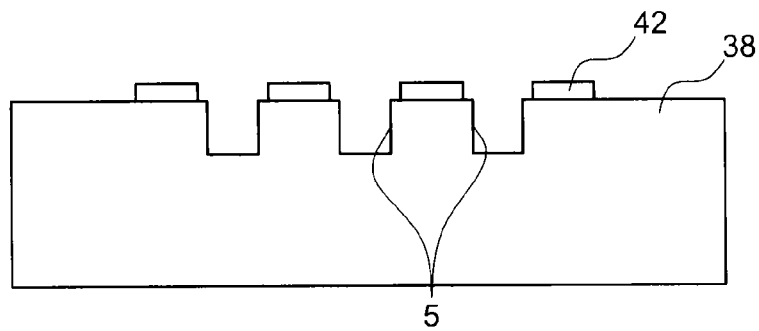

During a following step, a lithography and a development are carried out in order to structure the dry film, the latter then has beads along cavities etched in the cover. This can be a wide bead such as is shown in FIG. 7C, or more preferably several narrow beads parallel to one another such as is shown in FIGS. 2A to 2C. In this latter case, for example the beads and the spaces between the beads can be of a few μm to a few tens of micrometers.

More preferably, the beads have a regular structure and a close sealing surface over all of the structure to be sealed in such a way as to provide a homogeneous crushing of the dry film with a reasonable pressure during the step of sealing.

The element obtained as such is shown in FIG. 7C, the cover substrate 38 is then ready to be sealed on the substrate of the NEMS/MEMS structure 4.

Figure 8:
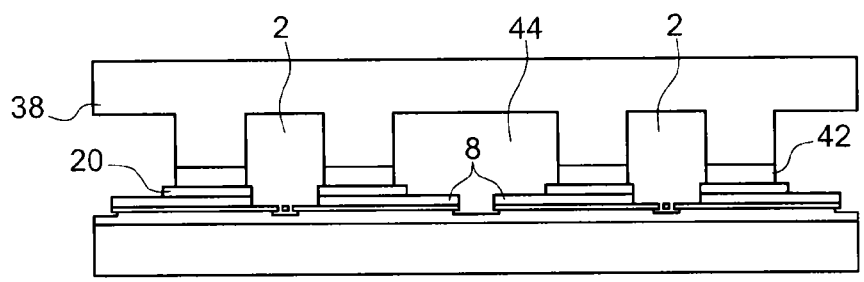

FIG. 8 shows the step of sealing of the cover substrate 38 and of the substrate 4 comprising the NEMS/MEMS structure. On this diagram and the following diagrams concerning the assembly of the two substrates and the separation of the elements in the case of a collective manufacture, a functionalisation layer on the surface of the NEMS (whether or not localised) is not implemented, but if such a functionalisation layer whether or not localised were implemented, the method for carrying out would be the same.

The sealing is carried out on a piece of sealing equipment which makes it possible to control the temperature and the pressure applied between the cover and the substrate to be sealed.

Surface treatments known in the state of the art can possibly be carried out in order to optimise the gluing energy.

During this step, the sealing of several covers 6 is carried out on a substrate comprising several NEMS/MEMS structures.

Firstly, the substrate 4 and the cover substrate 38 are aligned by means of the marks made previously on the substrates.

Then a pressure is applied between the substrate 4 and the cover substrate 38, as well as a temperature.

For example the pressure applied is of a magnitude of a few kN to a few tens of kN, and for example the temperature is between 100° C. and 200° C.

The substrate 4 and the cover substrate 38 are then assembled. The fluid channels are then sealed on lateral edges of the channels. The element obtained as such and shown in FIG. 8 comprises a plurality of fluid channel devices.

Typically, an assembly such as that of FIG. 8 is carried out using circular substrates used in microelectronics.

The steps of separating these channels shall now be described. In the case where a single device would have been carried out, the fluid channel device would be completed.

Figure 9A:
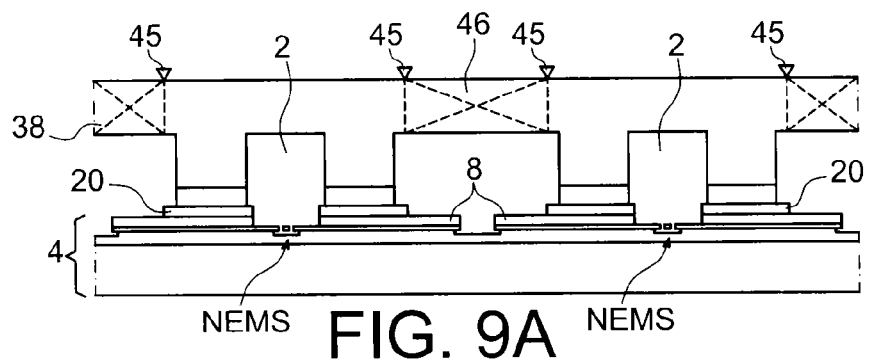

The method of separation first comprises a step of clearing the electric contact pads. According to the method of manufacture described hereinabove and as can be seen in FIG. 8 and FIG. 9A, the contact pads of a device located on one side of the channel 6 are adjacent to those of the adjacent device located on a side of the channel of the adjacent device.

These pads are therefore located in the same cavity 44 of the cover substrate 38.

The step of clearing the pads is therefore intended to open into the cavities 44 receiving the pads. This step is designated as STR (Saw To Reveal).

This step comprises the cutting of the substrate of the cover locally above the contact pads in such a way as to open into the cavities 44. The cutting marks 45 are symbolised by uninterrupted lines, with the cuts delimiting cut portions 46 which are removed.

This cutting is carried out in the planes XZ, as such the sawing residue does not penetrate into the channels.

Figure 9B:
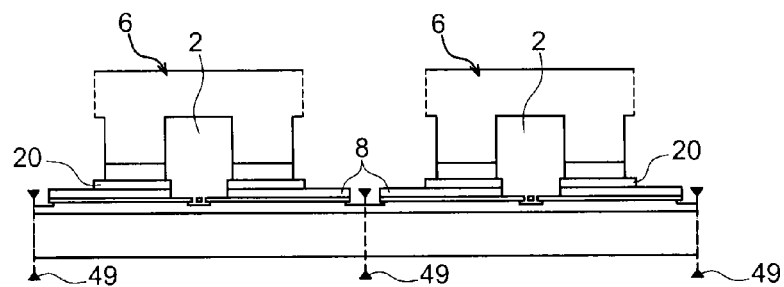
Figure 9C:
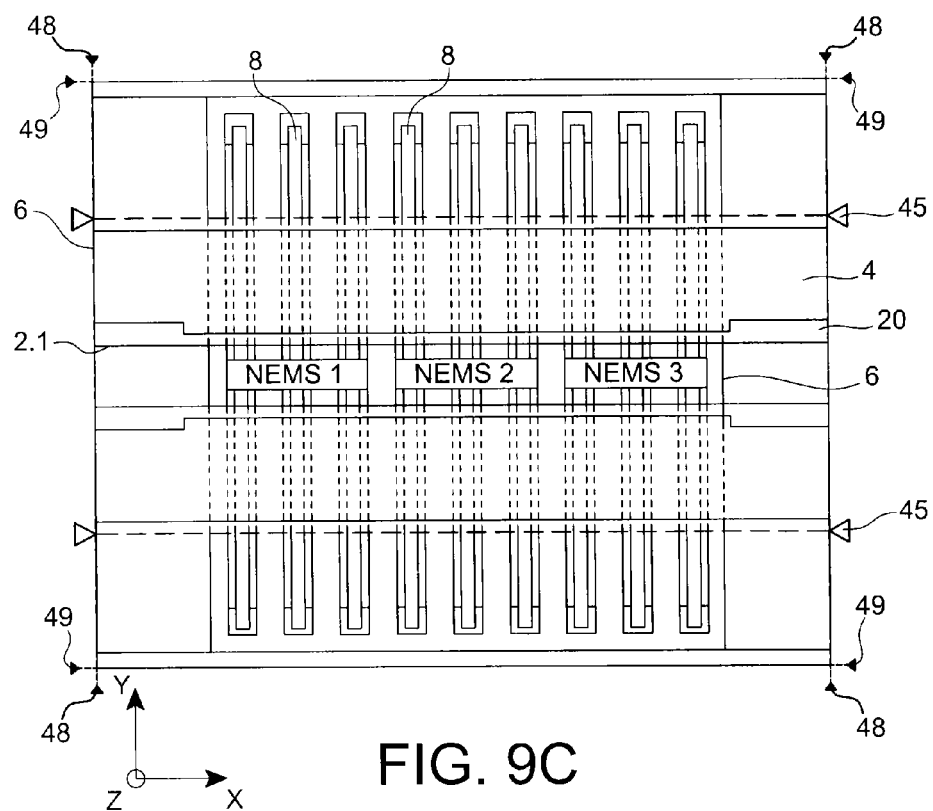

The element obtained as such is shown in FIG. 9B and FIG. 9C. The covers are now separated from one another. Note that for the understanding in FIG. 9C that the chips adjacent to the chip shown in figure are not indicated.

In the case where a functionalisation layer would have been deposited in a non-localised manner and would cover the contact pads located in the cavities 44, it is possible after removal of the substrate portions 46 to etch the portion of the functionalisation layer that covers the contact pads. This etching uses in a particularly advantageous manner the covers as a mask, as such providing an etching limited to the contact pads; with the portion of the functionalisation layer located on the NEMS/MEMS structures being protected by the covers.

A step of pre-cutting is then carried out of each cover and of the substrate 4 in the planes YZ according to a direction perpendicular to the direction X of the fluid channels solely in such a way as to longitudinally separate the devices with fluid channels.

These pre-cutting zones are symbolised by the arrows 48 in FIG. 9C.

In addition cutting or pre-cutting lines are also carried out in the substrate 4 in the planes XZ parallel to the direction X of the fluid channels in such a way as to transversally separate the devices with fluid channels.

These cutting or pre-cutting zones are symbolised by the arrows 49 in FIG. 9B.

Then, the devices with fluid channels are separated using the pre-cutting patterns 48 and 49, for example with cleavage, with laser cutting. More preferably, the sawing is avoided in what relates to the carrying out of the patterns 48 which would risk polluting the inside of the fluid channels.

This separation technique is particularly advantageous since it makes it possible to reveal the electric contact pads while still eliminating at the end of the production method any functionalisation layer present on the surface of these pads. In addition, it makes it possible to separate the chips from one another by preserving the integrity of the fluid channel.

It could be considered to use other techniques to reveal the electrical contact pads. For example, an etching could be considered of the cover substrate 38 to the pads or to a cavity formed beforehand above the contact pad. The substrate may not include a cavity 44 in the case where the substrate 38 is etched to the contact pads. But, more preferably, cavities 44 are provided as in FIG. 8, with the etching being stopped as soon as this opens in the cavities, which makes it possible to reveal the contacts. A polishing of the cover substrate can take place until opening into cavities formed beforehand above the contact pads, a technique designated as "grinding to reveal". In this case here it is suitable to have carried out cavities of the type 44 deeper than the cavities of the fluid channels to open into the cavities 44 without opening into the fluid channels in order to preserve their integrity.

Thanks to the invention, it is possible to carry out a fluid channel device comprising one or several mechanical structures suspended in the channel and one or several lateral electrical connections with a seal that is provided, as such preventing the formation of TSV in the substrate and also preventing the presence in the fluid channel of structures that provide the electrical contact between the mechanical structure which is located inside the channel and outside of this channel, of the metal pillar type extending the TSVs carried out in the cover or of the column type made of Si or glass with a cavity etched inside allowing for the wire-bonding on a pad of the mechanical structure insulated from the cavity, as is carried out conventionally with metal or polymer sealing approaches. In addition, the invention makes it possible to easily carry out networks of mechanical structures by allowing for a dense and complex electrical interconnection as close as possible to the mechanical structures with possibly several levels of metal. The invention can also make it possible to encapsulate all of the structures and layers present in the channel except the sensitive structures. Finally, it allows for the implementation of functionalisation during the method on suspended mechanical structures.

The invention claimed is:

1. A device comprising:
    a substrate comprising at least one microelectronic and/or nanoelectronic structure comprising at least one suspended portion,
    a cover,
    a fluid channel defined between said substrate and the cover, said fluid channel comprising two lateral walls and an upper wall connecting the two lateral walls formed by said cover and a lower wall formed by said substrate and at least two openings in order to provide a circulation in said channel, said microelectronic and/or nanoelectronic structure being located inside the fluid channel,
    an intermediate layer comprising a face in contact with base faces of said lateral walls, said face of the intermediate layer having an aptitude for sealing with the base faces,
    at least one electrical connection line extending between said microelectronic and/or nanoelectronic structure and the outside of the fluid channel, said connection line being carried out on the substrate and passing under one of the lateral walls, said at least one electrical connection line being at least partially covered by said intermediate layer at least immediately above the base face of said lateral wall, said lateral walls being sealingly fixed on said substrate by a sealing mechanism on said intermediate layer.

2. The device according to claim 1, comprising a functionalization layer encapsulating at least one portion of the suspended portion of the microelectronic and/or nanoelectronic structure.

3. The device according to claim 2, wherein the functionalization layer comprises one or several materials chosen from among organic or inorganic materials, polymers, oxides, semiconductors.

4. The device according to claim 1, wherein the at least one electrical connection line comprises at least one pair of connection lines extending laterally on either side of the microelectronic and/or nanoelectronic structure and each passing under a lateral wall.

5. The device according to claim 1, wherein the intermediate layer covers, in the fluid channel, the entire microelectronic and/or nanoelectronic structure except for its suspended portion.

6. The device according to claim 1, wherein the intermediate layer comprises an electrical insulating material, such as silicon oxide, or a silicon nitride.

7. The device according to claim 1, comprising electrical connection lines and contact pads, said contact pads being located outside of the fluid channel, said connection lines extending between the microelectronic and/or nanoelectronic structure and the contact pads.

8. The device according to claim 1, wherein the electrical connection lines comprise several levels of metallisation at least inside the fluid channel.

9. The device according to claim 1, comprising a dry film for sealing inserted between the intermediate layer and the base faces of the lateral walls of the cover.

10. The device according to claim 9, wherein the dry film for sealing is structured into several beads on interfaces between the intermediate layer and the base faces of the lateral walls.

11. The device according to claim 1, comprising at least one layer of material inserted between the intermediate layer and the base faces of the lateral walls creating a eutectic sealing or by thermo-compression, or by screen printing or wherein the sealing is a molecular sealing or wherein the sealing is made by glass frit.

12. The device according to claim 1, wherein the intermediate layer comprises a first layer of electrical insulating material in contact with the electrical connection line and a second layer deposited onto the first layer, said second layer being of a material such that it is little or not sensitive to a step of releasing the microelectronic and/or nanoelectronic structure.

13. The device according to claim 12, wherein the second layer is made of Si, silicon nitride, metal or hafnium oxide.

14. The device according to claim 1, wherein the channel forms a gas chromatography microcolumn.

15. A method of carrying out at least one device according to claim 1, comprising the steps of:
    a) carrying out the microelectronic and/or nanoelectronic structure on a substrate and of at least one connection line,
    b) forming of the intermediate layer is such a way that it has a substantially planar free face having an opening above said at least suspended portion
    c) carrying out of a cover substrate comprising a fluid channel,
    d) sealing of the cover substrate on the intermediate layer in such a way that the fluid channel is arranged facing the microelectronic and/or nanoelectronic structure.

16. The method according to claim 15, comprising a step of carrying out a functionalization layer inside the fluid channel on the microelectronic and/or nanoelectronic structure and/or on the walls of the cover and/or on the intermediate layer, said step being carried out before the sealing.

17. The method of carrying out according to claim 15, comprising after the step b), a step of releasing said microelectronic and/or nanoelectronic structure.

18. The method of carrying out according to claim 15, wherein the step of sealing using a dry film, the method for carrying out comprises the sub-steps of:
    rolling of dry film on the base faces of the walls of the cover,
    structuring of the dry film, coming closer together of the cover and of the substrate comprising the microelectronic and/or nanoelectronic structure, application of a pressure in such a way as to crush the dry film.

19. The method of carrying out according to claim 15, wherein the sealing is a eutectic sealing or by thermo-compression, or by molecular sealing or by screen printing.

20. The method of carrying out according to claim 15, wherein the carrying out of the intermediate layer takes place by deposit of a first layer of electrical insulating material and of deposit of a second layer on the first layer.

21. The method of carrying out according to claim 15, wherein several devices are carried out simultaneously, said substrate comprising several microelectronic and/or nanoelectronic structures and the cover substrate comprising several covers, with the covers being sealed simultaneously on the substrate comprising the microelectronic and/or nanoelectronic structures, in such a way that a fluid channel of a device can communicate or not with the fluid channel of other devices.

22. The method of carrying out according to claim 21, comprising the steps of:

carrying out pre-cuts in a direction perpendicular to the fluid channels in the cover substrate and in the substrate bearing the microelectronic structures and/or carrying out cuts or pre-cuts in a direction parallel to the fluid channels in the substrate bearing the microelectronic and/or nanoelectronic structures, separating devices.

23. The method of carrying out according to claim 22, wherein the separation of the devices is carried by cleavage.

24. The method of carrying out according to claim 22, wherein the cover substrate comprising cavities formed beforehand between the channels wherein are located contact pads after sealing, the method further comprises a step of cutting the cover substrate in order to open said cavities.

25. The method of carrying out according to claim 23, wherein the cover substrate comprising cavities formed beforehand between the channels wherein are located contact pads after sealing, the method further comprises a step of cutting the cover substrate in order to open said cavities.

26. The method of carrying out according to claim 24, wherein a functionalization layer has been formed on said microelectronic and/or nanoelectronic structure and on the contact pads before the sealing, said method comprising the step of removing by etching of the functionalisation layer on the contact pads after sealing and opening of the cavities in the cover, said covers forming masks to said etching for the microelectronic and/or nanoelectronic structures.

27. The method of carrying out according to claim 25, wherein a functionalization layer has been formed on said microelectronic and/or nanoelectronic structure and on the contact pads before the sealing, said method comprising the step of removing by etching of the functionalization layer on the contact pads after sealing and opening of the cavities in the cover, said covers forming masks to said etching for the microelectronic and/or nanoelectronic structures.

28. A method of carrying out at least one device according to claim 1, comprising the steps of:

a) carrying out the microelectronic and/or nanoelectronic structure on a substrate and of at least one connection line, b) forming of the intermediate layer in such a way that it has a substantially planar free face having an opening above said at least suspended portion c) carrying out of a cover substrate comprising a fluid channel, d) sealing of the cover substrate on the intermediate layer in such a way that the fluid channel is arranged facing the microelectronic and/or nanoelectronic structure, the method also comprising a step of carrying out a functionalization layer inside the fluid channel on the microelectronic and/or nanoelectronic structure and/or on the walls of the cover and/or on the intermediate layer, said step being carried out before the sealing.

* * * * *